US008071722B2

(12) United States Patent
Kaplan et al.

(10) Patent No.: US 8,071,722 B2
(45) Date of Patent: *Dec. 6, 2011

(54) SILK BIOMATERIALS AND METHODS OF USE THEREOF

(75) Inventors: David L. Kaplan, Concord, MA (US); Hyoung-Joon Jin, Seoul (KR); Gregory Rutledge, Newton, MA (US); Sergey Fridrikh, Acton, MA (US)

(73) Assignees: Trustees of Tufts College, Medford, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/688,014

(22) Filed: Jan. 15, 2010

(65) Prior Publication Data

US 2010/0196447 A1   Aug. 5, 2010

Related U.S. Application Data

(63) Continuation of application No. 11/020,650, filed on Dec. 23, 2004, now Pat. No. 7,674,882, which is a continuation of application No. PCT/US03/19968, filed on Jun. 24, 2003.

(60) Provisional application No. 60/390,929, filed on Jun. 24, 2002, provisional application No. 60/402,738, filed on Aug. 12, 2002, provisional application No. 60/430,291, filed on Dec. 2, 2002.

(51) Int. Cl.
*A61K 38/00* (2006.01)
*C07K 14/00* (2006.01)

(52) U.S. Cl. ............................................ 530/353; 514/2
(58) Field of Classification Search .......................... None
See application file for complete search history.

(56) References Cited

U.S. PATENT DOCUMENTS

| 1,989,005 | A | 1/1935 | Fink et al. |
| 4,233,212 | A | 11/1980 | Otoi et al. |
| 5,047,507 | A | 9/1991 | Buchegger et al. |
| 5,290,494 | A | 3/1994 | Coombes et al. |
| 5,606,019 | A | 2/1997 | Cappello |
| 5,770,193 | A | 6/1998 | Vacanti et al. |
| 6,110,590 | A | 8/2000 | Zarkoob et al. |
| 6,175,053 | B1 | 1/2001 | Tsubouchi |
| 6,592,623 | B1 | 7/2003 | Bowlin et al. |
| 6,815,427 | B2 | 11/2004 | Tsubouchi |
| 6,902,932 | B2 * | 6/2005 | Altman et al. ............... 435/395 |
| 7,057,023 | B2 | 6/2006 | Islam et al. |
| 7,285,637 | B2 | 10/2007 | Armato et al. |
| 7,635,755 | B2 | 12/2009 | Kaplan |
| 7,662,409 | B2 * | 2/2010 | Masters .......................... 424/484 |
| 7,674,882 | B2 * | 3/2010 | Kaplan et al. ................. 530/353 |
| 7,727,575 | B2 | 6/2010 | Kaplan |
| 7,842,780 | B2 | 11/2010 | Kaplan |
| 2002/0028243 | A1 | 3/2002 | Masters |
| 2004/0005363 | A1 | 1/2004 | Tsukada et al. |
| 2004/0266992 | A1 | 12/2004 | Migliaresi et al. |
| 2007/0212730 | A1 | 9/2007 | Vepari et al. |
| 2008/0085272 | A1 | 4/2008 | Kaplan et al. |
| 2008/0293919 | A1 | 11/2008 | Huang et al. |
| 2009/0202614 | A1 | 8/2009 | Kaplan et al. |
| 2009/0232963 | A1 | 9/2009 | Murphy et al. |
| 2009/0234026 | A1 | 9/2009 | Kaplan et al. |
| 2010/0028451 | A1 | 2/2010 | Kaplan |
| 2010/0046902 | A1 | 2/2010 | Georgakoudi et al. |
| 2010/0055438 | A1 * | 3/2010 | Kaplan et al. ................. 428/221 |
| 2010/0063404 | A1 | 3/2010 | Georgakoudi et al. |
| 2010/0065784 | A1 | 3/2010 | Georgakoudi et al. |
| 2010/0068740 | A1 | 3/2010 | Perry et al. |
| 2010/0070068 | A1 | 3/2010 | Georgakoudi et al. |
| 2010/0096763 | A1 | 4/2010 | Georgakoudi et al. |
| 2010/0120116 | A1 | 5/2010 | Kaplan |
| 2010/0178304 | A1 | 7/2010 | Kaplan et al. |
| 2010/0191328 | A1 | 7/2010 | Marchant et al. |
| 2010/0196447 | A1 | 8/2010 | Kaplan et al. |

FOREIGN PATENT DOCUMENTS

| JP | 58-38449 | 8/1983 |
| JP | 06-346314 | 12/1994 |
| JP | 10-36676 | 2/1998 |
| JP | 2000-273264 | 10/2000 |
| JP | 2004068161 | 3/2004 |
| WO | 99/01089 | 1/1999 |
| WO | 01/36531 A1 | 5/2001 |
| WO | 01/56626 A1 | 8/2001 |
| WO | 02072931 | 9/2002 |
| WO | 03022909 | 3/2003 |
| WO | 2004041845 | 5/2004 |

OTHER PUBLICATIONS

Chen et al., J Appl Polymer Sci, 65:2257-2262 (1997). "pH Sensitivity and Ion Sensitivity of Hydrogels Based on Complex-Forming Chitosan/Silk Fibroin Interpenetrating Polymer Network."
Computer translation of JP 2004068161 A (Translated May 13, 2009).
Demura et al., Biosensors, pp. 361-372 (1989). "Immobilization of Biocatalysts with Bombyx mori Silk Fibroin by Several Kinds of Physical Treatment and its Application to Glucose Sensors."
Doshi et al., J Electrostatics, 35:151-160 (1995). "Electrospinning Process and Applications of Electrospun Fibers."
Huang et al., Macromolecules, 33:2989-2997 (2000). "Generation of SyntheticElastin-Mimetic Small Diameter Fibers and Fiber Networks."

(Continued)

*Primary Examiner* — Anand Desai
(74) *Attorney, Agent, or Firm* — Nixon Peabody LLP

(57) ABSTRACT

The present invention provides an all-aqueous process and composition for production of silk biomaterials, e.g., fibers, films, foams and mats. In the process, at least one biocompatible polymer, such as poly(ethylene oxide) (PEO) (a well-documented biocompatible material), was blended with the silk protein prior to processing e.g., electrospinning. We discovered that this step avoids problems associated with conformational transitions of fibroin during solubilization and reprocessing from aqueous solution which lead to embrittled materials. Moreover, the process avoids the use of organic solvents that can pose problems when the processed biomaterials are exposed to cells in vitro or in vivo.

19 Claims, 16 Drawing Sheets

OTHER PUBLICATIONS

Huang et al., J Biomater Sci Polymer Edn, 12(9):979-993 (2001). "Engineered collagen-PEO nanofibers and fabrics."

Jin et al., Biomacromolecules, 3:1233-1239 (2002). "Electrospinning Bombyx mori Silk with Poly(ethylene oxide)."

Kweon et al., J Appl Polymer Sci, 80:1848-1853 (2001). "Preparation of Semi-Interpreting Polymer Networks Composed of Silk Fibroin and Poly(ethylene glycol) Macromer."

Lazaris et al., Science, 295:472-476 (2002). "Spider silk fibers spun from soluble recombinant silk produced in mammalian cells."

Liang et al., J Appl Polymer Sci, 45:1937-1943 (1992). "Improvements of the Physical Properties of Fibroin Membranes with Sodium Alginate."

Reneker et al., Nanotechnology, 7:216-223 (1996). "Nanometer Diameter Fibers of Polymer, Produced by Electrospinning."

Demura, et al., Porous Membrane of Bombyx mori silk fibroin: structure characterization, physical properties and application to glucose oxidase immobilization, J. Membrane Science 59:32-52 (1991).

Foreign Counterpart Application EP 03761306: Supplementary European Search Report issued Sep. 14, 2010.

Asakura et al., Macromolecules, 18:1841-1845 (1985). "Conformational characterization of B. Mori Silk Fibroin in the Solid State by High-Frequency 13C Cross Polarization-Magic Angel Spinning NMR, X-ray Diffraction and Infrared Spectroscopy."

Chen et al., "Conformation Transition Kinetics of Bombyx mori Silk Protein," Proteins: Structure, Function, and Bioinformatics 68:223-231 (2007).

Database WPI Week 198205, Derwent Publications Ltd., London, GB; AN 1982-09092E & JP 56 166235 A Dec. 21, 1981 Abstract.

Derwent Record, Abstract of JP08295697 A2 "Production of Aqueous Solution of Silk Fibroin At High Concentration," Nov. 12, 1996.

U.S. Appl. No. 60/906,509, filed Mar. 13, 2007 by Perry et al.
U.S. Appl. No. 61/224,618, filed Jul. 10, 2009 by Perry et al.
U.S. Appl. No. 12/672,521, filed Feb. 8, 2010 by Wang.
U.S. Appl. No. 12/866,256, filed Nov. 4, 2010 by Kaplan et al.
U.S. Appl. No. 12/741,066, filed May 3, 2010 by Omenetto et al.
U.S. Appl. No. 12/934,666, filed Sep. 27, 2010 by Vunjak-Novakovic et al.
U.S. Appl. No. 12/991,973, filed Nov. 10, 2010 by Kaplan et al.
U.S. Appl. No. 12/999,087, filed Dec. 15, 2010 by Kaplan et al.
U.S. Appl. No. 12/974,796, filed Dec. 21, 2010 by Kaplan et al.
Patent Abstracts of Japan, JP 01118544, Nov. 5, 1989, Abstract.

* cited by examiner

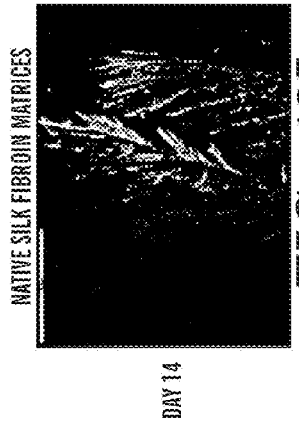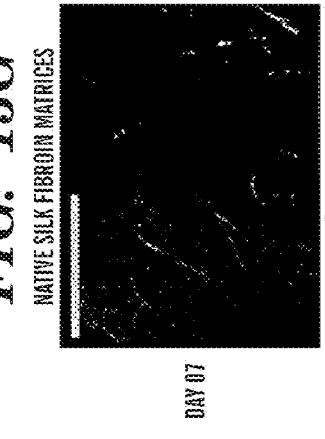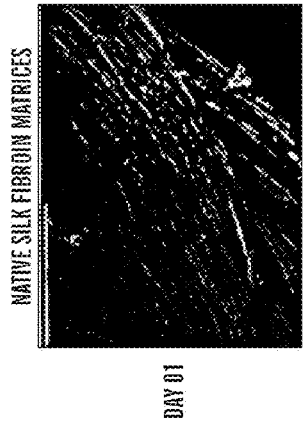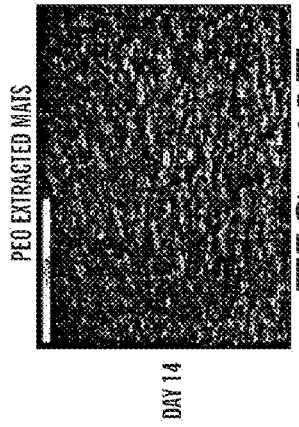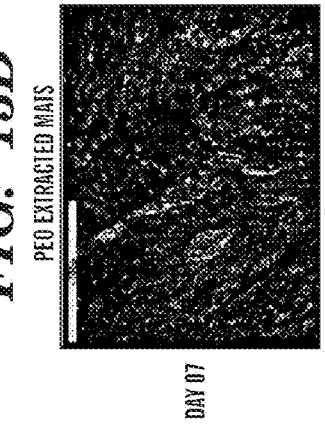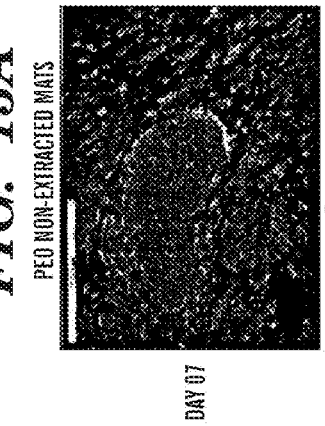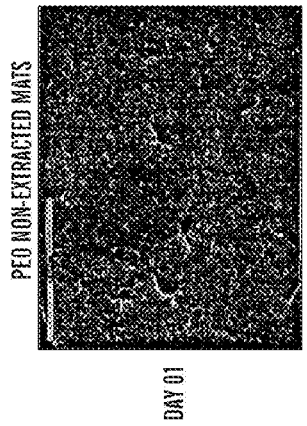

SILK BIOMATERIALS AND METHODS OF USE THEREOF

CROSS-REFERENCE TO RELATED APPLICATIONS

This application is a Continuation of U.S. patent application Ser. No. 11/020,650 filed on Dec. 23, 2004, which is a Continuation of International Application No. PCT/US2003/019968 filed on Jun. 24, 2003, which designated the United States and which claims the benefit of priority under 35 U.S.C. §119(e) of U.S. Provisional Application Nos. 60/390,929 filed on Jun. 24, 2002, 60/402,738 filed on Aug. 12, 2002, and 60/430,291 filed on Dec. 2, 2002, the contents of which are incorporated herein by reference in their entireties.

GOVERNMENT SUPPORT

The subject matter of this application was made with support from the United States Government, National Institutes of Health (NIH) grant R01 DE13405-01A1, National Science Foundation grant DMR0090384, and United States Air Force grant F49620-01-C-0064.

FIELD OF THE INVENTION

The present invention relates generally to silk biomaterials, e.g., fibers, films, foams and mats, and use of those materials in tissue engineered constructs.

BACKGROUND OF THE INVENTION

Electrospinning for the formation of fine fibers has been actively explored recently for applications such as high performance filters [1,2] and biomaterial scaffolds for cell growth, vascular grafts, wound dressings or tissue engineering [2-4]. Fibers with nanoscale diameter provide benefits due to their high surface area. In this electrostatic technique, a strong electric field is generated between a polymer solution contained in a glass syringe with a capillary tip and a metallic collection screen. When the voltage reaches a critical value, the charge overcomes the surface tension of the deformed drop of suspended polymer solution formed on the tip of the syringe, and a jet is produced. The electrically charged jet undergoes a series of electrically induced bending instabilities during passage to the collection screen that results in stretching [5-7]. This stretching process is accompanied by the rapid evaporation of the solvent and results in a reduction in the diameter of the jet [8-12]. The dry fibers accumulated on the surface of the collection screen form a non-woven mesh of nanometer to micrometer diameter fibers even when operating with aqueous solutions at ambient temperature and pressure. The electrospinning process can be adjusted to control fiber diameter by varying the charge density and polymer solution concentration, while the duration of electrospinning controls the thickness of the deposited mesh [8-13].

Protein fiber spinning in nature, such as for silkworm and spider silks, is based on the formation of concentrated solutions of metastable lyotropic phases that are then forced through small spinnerets into air [14]. The fiber diameters produced in these natural spinning processes range from tens of microns in the case of silkworm silk to microns to submicron in the case of spider silks [14]. The production of fibers from protein solutions has typically relied upon the use of wet or dry spinning processes [15, 16]. Electrospinning offers an alternative approach to protein fiber formation that can potentially generate very fine fibers. This would be a useful feature based on the potential role of these types of fibers in some applications such as biomaterials and tissue engineering [17]. Electrospinning has been utilized to generate nanometer diameter fibers from recombinant elastin protein [17] and silk-like protein [18-20]. Zarkoob et al. [21] have also reported that silkworm silk from *Bombyx mori* cocoons and spider dragline silk from *Nephila clavipes* silk can be electrospun into nanometer diameter fibers if first solubilized in the organic solvent hexafluoro-2-propanol (REP).

Silk is a well described natural fiber produced by the silkworm, *Bombyx mori*, which has been used traditionally in the form of threads in textiles for thousands of years. This silk contains a fibrous protein termed fibroin (both heavy and light chains) that form the thread core, and glue-like proteins termed sericin that surround the fibroin fibers to cement them together. The fibroin is a highly insoluble protein containing up to 90% of the amino acids glycine, alanine and serine leading to β-pleated sheet formation in the fibers [22].

The unique mechanical properties of reprocessed silk such as fibroin and its biocompatibility make the silk fibers especially attractive for use in biotechnological materials and medical applications [14, 23].

Electrospinning silk fibers for biomedical applications is a complicated process, especially due to problems encountered with conformational transitions of silkworm fibroin during solubilization and reprocessing from aqueous solution to generate new fibers and films. The problem with conformation transition is due to the formation of β-sheets which result in embrittled materials. Additionally, organic solvents typically used in silk electrospinning, as well as foam, film or mesh formation, pose biocompatibility problems when the processed materials are exposed to cells in vitro or in vivo.

Silk blends have been extensively studied with respect to film formation. Blends with polyacrylamide [26], sodium alginate [27], cellulose [28,35], chitosan [29,36,37], poly (vinyl alcohol) [30,38,39], acrylic polymers [31], poly(ethylene glycol) (300 g/mol [40] or 8,000 g/mol [41]) poly(ε-caprolactone-co-D,L-lactide) [42], and S-carboxymethyl keratin [43] have been studied to improve the mechanical or thermal stability or membrane properties of silk films.

Unfortunately, none of these blends have proven successful in overcoming problems associated with processing or reprocessing silk protein, e.g., embrittlement, and, therefore, new methods, especially organic solvent free methods, are needed.

SUMMARY OF THE INVENTION

The present invention provides an all-aqueous process for production of silk biomaterials, e.g., fibers, films, foams and mats. In the process, at least one biocompatible polymer, such as poly(ethylene oxide) (PEO), was blended with the silk protein prior to processing e.g., electrospinning. We discovered that this step avoids problems associated with conformational transitions of fibroin during solubilization and reprocessing from aqueous solution which lead to embrittled materials. Moreover, the process avoids the use of organic solvents that can pose problems when the processed biomaterials are exposed to cells in vitro or in vivo.

In one embodiment, the biomaterial is a fiber. The fiber is produced by a process comprising the steps of (a) preparing an aqueous solution of a silk protein; (b) adding a biocompatible polymer to the aqueous solution; and (c) electrospinning the solution. The process may further comprise step (d) of immersing the fiber into an alcohol/water solution. The alcohol is preferably methanol, ethanol, isopropyl alcohol (2-propanol) or n-butanol. Methanol is most preferred. Additionally, the process may further comprise step (e) of washing the fibroin fiber in water.

The present invention also provides a fiber produced by the process.

In another embodiment, the biomaterial is a film. The film is produced, for example, by a process comprising the steps of (a) preparing an aqueous solution of a silk protein; (b) adding a biocompatible polymer to the aqueous solution; (c) drying the mixture; and (d) contacting the mixture with an alcohol/water solution to crystallize the silk blend film. The process can optionally include step (e) of drawing or mono-axially stretching the resulting film to alter or enhance its mechanical properties.

In the processes of the present invention, the aqueous solution of a silk protein is preferably in an aqueous salt solution (e.g., lithium bromide or lithium thiocyanate) or a strong acid solution (e.g., formic acid, hydrochloric acid).

The silk protein suitable for use in the present invention is preferably fibroin or related proteins (i.e., silks from spiders). The fibroin or related proteins are preferably obtained from a solution containing a dissolved silkworm silk or spider silk. The silkworm silk is obtained, for example, from *Bombyx mori*. Spider silk may be obtained from *Nephila clavipes*. In the alternative, the silk protein suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012.

The present invention also provides a biomaterial comprising a silk protein and a biocompatible polymer. The biomaterial may be a fiber, film, foam or a non-woven network of fibers (also referred to as a mat). The biomaterial may be used to facilitate tissue repair, ingrowth or regeneration as scaffold in a tissue engineered biocompatible polymer engineered construct, or to provide delivery of a protein or therapeutic agent.

As used herein, biocompatible means that the polymer is non-toxic, non-mutagenic, and elicits a minimal to moderate inflammatory reaction. Preferred biocompatible polymer for use in the present invention include, for example, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, and polyanhydrides. In accordance with the present invention, two or more biocompatible polymers can be added to the aqueous solution.

The present invention further provides a composition comprising a silk protein and a biocompatible polymer in water, wherein the composition is free of solvents other than water. Preferably, the silk protein is fibroin and the biocompatible polymer is PEO. The composition is useful in the methods of the present invention.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

FIGS. 5A-13B show percentage weight loss of silk and PEO blend films in water at 37° C. (dotted line: calculated silk weight in films): (13A) silk/PEO blend and (13B) silk/PEG blend.

FIG. 6 shows DSC thermograms of silk, PEO and silk/PEO blend films before methanol treatment: (a) silk film; (b) silk/PEO (98/2) blend; (c) silk/PEO (90/10) blend; (d) silk/PEO (80/20) blend; (e) silk/PEO (70/30) blend; (f) silk/PEO (60/40) blend; and (g) PEO.

FIG. 7 show DSC thermograms of silk/PEO blend films after methanol treatment: (a) silk film; (b) silk/PEO (98/2) blend; (c) silk/PEO (90/10) blend; (d) silk/PEO (80/20) blend; (e) silk/PEO (70/30) blend; and (f) silk/PEO (60/40) blend.

FIG. 9 show differential scanning calorimeter (DSC) thermograms of silk/PEO electrospun fiber mats after methanol treatment: (a) PEO non-extracted mat and (b) PEO extracted mat.

FIG. 11 shows representative mechanical properties of electrospun fibers.

FIGS. 12A-12B show phase-contrast microscopy images of BMSCs growing on tissue culture plastic (poly(styrene)) after 1 day of culture in the presence of (a) PEO non-extracted mats and (b) PEO extracted mats (×40, scale bar: 100 μm).

FIGS. 13A-I show scanning electron micrographs of BMSCs growing on electrospun mats and native silk fibroin matrices after 1, 7, and 14 days (scale bar: 500 μM); FIGS. 13A-13C PEO non-extracted mats at day 1, 7, and 14, respectively. FIGS. 13D-13F PEO extracted mats at day, 1, 7, and 14 respectively. FIGS. 13G-13H native silk fibroin matrices at day 1, 7, and 14, respectively.

DETAILED DESCRIPTION OF THE INVENTION

Figure 1:
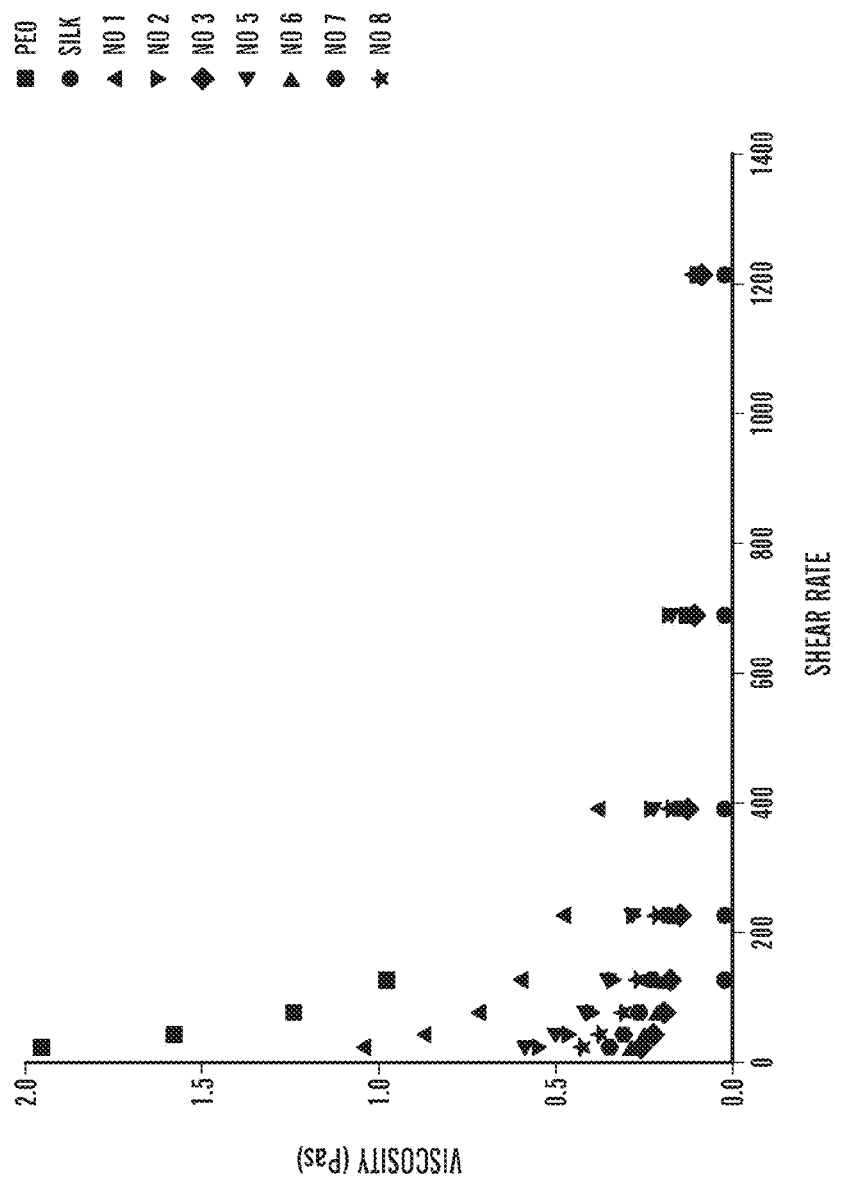
FIG. 1 illustrates shear viscosities of silk/PEO blend solutions in water.

We have developed an all-aqueous process for producing silk biomaterials, e.g., electrospun silk fibers, films, foams and mats. This process effectively avoids the problems of (1) poor biocompatibility due to organic solvents used and (2) embrittled materials associated with conformational transitions of silk protein (e.g., silkworm fibroin) during solubilization and reprocessing from an aqueous solution. The process of the present invention comprises adding a biocompatible polymer to an aqueous solution of a silk protein. The solution is then processed to form a silk biomaterial.

The silk protein suitable for use in the present invention is preferably fibroin or related proteins (i.e., silks from spiders). Preferably, fibroin or related proteins are obtained from a solution containing a dissolved silkworm silk or spider silk. The silkworm silk is obtained, for example, from *Bombyx mori*. Spider silk may be obtained from *Nephila clavipes*. In the alternative, the silk protein suitable for use in the present invention can be obtained from a solution containing a genetically engineered silk, such as from bacteria, yeast, mammalian cells, transgenic animals or transgenic plants. See, for example, WO 97/08315 and U.S. Pat. No. 5,245,012.

The silk protein solution can be prepared by any conventional method known to one skilled in the art. For example, *B. mori* cocoons are boiled for about 30 minutes in an aqueous solution. Preferably, the aqueous solution is about 0.02M $Na_2CO_3$. The cocoons are rinsed, for example, with water to extract the sericin proteins and the extracted silk is dissolved in an aqueous salt solution. Salts useful for this purpose include, lithium bromide, lithium thiocyanate, calcium nitrate or other chemical capable of solubilizing silk. A strong acid such as formic or hydrochloric may also be used. Preferably, the extracted silk is dissolved in about 9-12 M LiBr solution. The salt is consequently removed using, for example, dialysis.

The biocompatible polymer preferred for use in the present invention is selected from the group comprising polyethylene oxide (PEO) (U.S. Pat. No. 6,302,848) [24], polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), polyanhydrides (U.S. Pat. No. 5,270,419), and other biocompatible polymers. Preferably, the PEO has a molecular weight from 400,000 to 2,000,000 g/mol. More preferably, the molecular weight of the PEO is about 900,000 g/mol. As contemplated by the present invention, two or more biocompatible polymers can be directly added to the aqueous solution simultaneously.

The present invention, in one embodiment, provides a fiber produced by a process of preparing an aqueous solution of a silk protein, adding a biocompatible polymer to the aqueous solution, and electrospinning the solution, thereby forming the fiber. Preferably, the fiber has a diameter in the range from 50 to 1000 nm.

In this embodiment, the aqueous solution preferably has a concentration of about 0.1 to about 25 weight percent of the silk protein. More preferably, the aqueous solution has a concentration of about 1 to about 10% weight percent of the silk protein.

While not wishing to be bound by theory, it is believed that the addition of a biocompatible polymer or a plurality of biocompatible polymers described above generates viscosity and surface tension suitable for electrospinning.

Electrospinning can be performed by any means known in the art (see, for example, U.S. Pat. No. 6,110,590). Preferably, a steel capillary tube with a 1.0 mm internal diameter tip is mounted on an adjustable, electrically insulated stand. Preferably, the capillary tube is maintained at a high electric potential and mounted in the parallel plate geometry. The capillary tube is preferably connected to a syringe filled with silk/biocompatible polymer solution. Preferably, a constant volume flow rate is maintained using a syringe pump, set to keep the solution at the lip of the tube without dripping. The electric potential, solution flow rate, and the distance between the capillary tip and the collection screen are adjusted so that a stable jet is obtained. Dry or wet fibers are collected by varying the distance between the capillary tip and the collection screen.

A collection screen suitable for collecting silk fibers can be a wire mesh, a polymeric mesh, or a water bath. Alternatively and preferably, the collection screen is an aluminum foil. The aluminum foil can be coated with Teflon fluid to make peeling off the silk fibers easier. One skilled in the art will be able to readily select other means of collecting the fiber solution as it travels through the electric field. As is described in more detail in the Examples section below, the electric potential difference between the capillary tip and the aluminum foil counter electrode is, preferably, gradually increased to about 12 kV, however, one skilled in the art should be able to adjust the electric potential to achieve suitable jet stream.

The process of the present invention may further comprise steps of immersing the spun fiber into an alcohol/water solution to induce crystallization of silk. The composition of alcohol/water solution is preferably 90/10 (v/v). The alcohol is preferably methanol, ethanol, isopropyl alcohol (2-propanol) or n-butanol. Methanol is most preferred. Additionally, the process may further comprise the step of washing the fibroin fiber in water.

In another embodiment, the biomaterial is a film. The process for forming the film comprises, for example, the steps of (a) preparing an aqueous silk fibroin solution comprising silk protein; (b) adding a biocompatible polymer to the aqueous solution; (c) drying the mixture; and (d) contacting the dried mixture with an alcohol (preferred alcohols are listed above) and water solution to crystallize a silk blend film. Preferably, the biocompatible polymer is poly(ethylene oxide) (PEO). The process for producing the film may further include step (e) of drawing or mono-axially stretching the resulting silk blend film to alter or enhance its mechanical properties. The stretching of a silk blend film induces molecular alignment in the fiber structure of the film and thereby improves the mechanical properties of the film [46-49].

In a preferred embodiment, the film comprises from about 50 to about 99.99 part by volume aqueous silk protein solution and from about 0.01 to about 50 part by volume PEO. Preferably, the resulting silk blend film is from about 60 to about 240 µm thick, however, thicker samples can easily be formed by using larger volumes or by depositing multiple layers.

In a further embodiment, the biomaterial is a foam. Foams may be made from methods known in the art, including, for example, freeze-drying and gas foaming in which water is the solvent or nitrogen or other gas is the blowing agent, respectively.

In one embodiment, the foam is a micropatterned foam. Micropatterned foams can be prepared using, for example, the method set forth in U.S. Pat. No. 6,423,252, the disclosure of which is incorporated herein by reference.

For example, the method comprising contacting the silk protein/biocompatible polymer solution with a surface of a mold, the mold comprising on at least one surface thereof a three-dimensional negative configuration of a predetermined micropattern to be disposed on and integral with at least one surface of the foam, lyophilizing the solution while in contact with the micropatterned surface of the mold, thereby providing a lyophilized, micropatterned foam, and removing the lyophilized, micropatterned foam from the mold. Foams prepared according this method comprise a predetermined and designed micropattern on at least one surface, which pattern is effective to facilitate tissue repair, ingrowth or regeneration, or is effective to provide delivery of a protein or a therapeutic agent.

In another embodiment, the biomaterial is a scaffold produced using a molding process. See, for example, WO 03/004254 and WO 03/022319. Using such a process, for example, the silk protein/biocompatible polymer solution is placed into a mold, the mold being a negative of the desired shape of the scaffold. The solution is cured and removed from the mold. In certain embodiments, it may be desirable to form pores in the polymer using, for example, particulate leaching and other methods known in the art.

Additional biomaterials may be formed with the composition of the present invention using ink jet printing of patterns, dip pen nanolithography patterns and microcontact printing. See, Wilran et al., (2001) PNAS 98:13660-13664 and the references cited therein.

The biomaterials produced by the processes of the present invention may be used in a variety of medical applications such as wound closure systems, including vascular wound repair devices, hemostatic dressings, patches and glues, sutures, drug delivery and in tissue engineering applications, such as, for example, scaffolding, ligament prosthetic devices and in products for long-term or bio-degradable implantation into the human body. A preferred tissue engineered scaffold is a non-woven network of electrospun fibers.

Additionally, these biomaterials can be used for organ repair replacement or regeneration strategies that may benefit from these unique scaffolds, including but are not limited to, spine disc, cranial tissue, dura, nerve tissue, liver, pancreas, kidney, bladder, spleen, cardiac muscle, skeletal muscle, tendons, ligaments and breast tissues.

In another embodiment of the present invention, silk biomaterials can contain therapeutic agents. To form these materials, the polymer would be mixed with a therapeutic agent prior to forming the material or loaded into the material after it is formed. The variety of different therapeutic agents that can be used in conjunction with the biomaterials of the present invention is vast. In general, therapeutic agents which may be administered via the pharmaceutical compositions of the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-.beta.I-III), vascular endothelial growth factor (VEGF)); and other naturally derived or genetically engineered proteins, polysaccharides, glycoproteins, or lipoproteins. These growth factors are described in The Cellular and Molecular Basis of Bone Formation and Repair by Vicki Rosen and R. Scott Thies, published by R. G. Landes Company hereby incorporated herein by reference.

Silk biomaterials containing bioactive materials may be formulated by mixing one or more therapeutic agents with the polymer used to make the material. Alternatively, a therapeutic agent could be coated on to the material preferably with a pharmaceutically acceptable carrier. Any pharmaceutical carrier can be used that does not dissolve the foam. The therapeutic agents, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the material. Upon contact with body fluids the drug will be released.

The biocompatible polymer may be extracted from the biomaterial prior to use. This is particularly desirable for tissue engineering applications. Extraction of the biocompatible polymer may be accomplished, for example, by soaking the biomaterial in water prior to use.

The tissue engineering scaffolds biomaterials can be further modified after fabrication. For example, the scaffolds can be coated with bioactive substances that function as receptors or chemoattractors for a desired population of cells. The coating can be applied through absorption or chemical bonding.

Additives suitable for use with the present invention include biologically or pharmaceutically active compounds. Examples of biologically active compounds include cell attachment mediators, such as the peptide containing variations of the "RGD" integrin binding sequence known to affect cellular attachment, biologically active ligands, and substances that enhance or exclude particular varieties of cellular or tissue ingrowth. Such substances include, for example, osteoinductive substances, such as bone morphogenic proteins (BMP), epidermal growth factor (EGF), fibroblast growth factor (FGF), platelet-derived growth factor (PDGF), vascular endothelial growth factor (VEGF), insulin-like growth factor (IGF-I and II), TGF-, YIGSR peptides, glycosaminoglycans (GAGs), hyaluronic acid (HA), integrins, selectins and cadherins.

The scaffolds are shaped into articles for tissue engineering and tissue guided regeneration applications, including reconstructive surgery. The structure of the scaffold allows generous cellular ingrowth, eliminating the need for cellular pre-seeding. The scaffolds may also be molded to form external scaffolding for the support of in vitro culturing of cells for the creation of external support organs.

The scaffold functions to mimic the extracellular matrices (ECM) of the body. The scaffold serves as both a physical support and an adhesive substrate for isolated cells during in vitro culture and subsequent implantation. As the transplanted cell populations grow and the cells function normally, they begin to secrete their own ECM support.

In the reconstruction of structural tissues like cartilage and bone, tissue shape is integral to function, requiring the molding of the scaffold into articles of varying thickness and shape. Any crevices, apertures or refinements desired in the three-dimensional structure can be created by removing portions of the matrix with scissors, a scalpel, a laser beam or any other cutting instrument. Scaffold applications include the regeneration of tissues such as nervous, musculoskeletal, cartilaginous, tendenous, hepatic, pancreatic, ocular, integumenary, arteriovenous, urinary or any other tissue forming solid or hollow organs.

The scaffold may also be used in transplantation as a matrix for dissociated cells, e.g., chondrocytes or hepatocytes, to create a three-dimensional tissue or organ. Any type of cell can be added to the scaffold for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells, bone marrow cells, skin cells, pluripotent cells and stem cells, and combination thereof, either as obtained from donors, from established cell culture lines, or even before or after genetic engineering. Pieces of tissue can also be used, which may provide a number of different cell types in the same structure.

The cells are obtained from a suitable donor, or the patient into which they are to be implanted, dissociated using standard techniques and seeded onto and into the scaffold. In vitro culturing optionally may be performed prior to implantation. Alternatively, the scaffold is implanted, allowed to vascularize, then cells are injected into the scaffold. Methods and reagents for culturing cells in vitro and implantation of a tissue scaffold are known to those skilled in the art.

The biomaterials of the present intention may be sterilized using conventional sterilization process such as radiation based sterilization (i.e. gamma-ray), chemical based sterilization (ethylene oxide) or other appropriate procedures. Preferably the sterilization process will be with ethylene oxide at a temperature between 52-55° C. for a time of 8 hours or less. After sterilization the biomaterials may be packaged in an appropriate sterilize moisture resistant package for shipment and use in hospitals and other health care facilities.

The invention will be further characterized by the following examples which are intended to be exemplary of the invention.

EXAMPLES

Example I

Materials

Cocoons of *B. mori* silkworm silk supplied by Institute of Sericulture, Tsukuba, Japan. PEO with an average molecular weight of 4×105 g/mol and 9×105 g/mol (Aldrich) were used in blending.

Preparation of Regenerated *B. mori* Silk Fibroin Solutions

*B. mori* silk fibroin was prepared as follows as a modification of our earlier procedure [25]. Cocoons were boiled for 30 min in an aqueous solution of 0.02 M Na2CO3, then rinsed thoroughly with water to extract the glue-like sericin proteins. The extracted silk was then dissolved in 12 M LiBr solution at 60° C. yielding a 20% (w/v) solution. This solution was dialyzed in water using a Slide-a-Lyzer dialysis cassette (Pierce, MWCO 2000). The final concentration of aqueous silk solution was 3.0 to 7.2 wt %, which was determined by weighing the remaining solid after drying. HFIP silk solution (1.5 wt %) was prepared by dissolving the silk fibroin produced after lyophilizing the aqueous silk solution into the HFIP.

Preparation of Spinning Solutions

Silk/PEO blends in water were prepared by adding PEO (900,000 g/mol) directly into the silk aqueous solutions generating 4.8 to 8.8 wt % silk/PEO solutions. Silk solution in HFIP (1.5 wt %) and PEO (4.0 wt %) solution in water, respectively, were also prepared as control solutions for comparisons with the blend systems. Silk solution in HFIP was prepared by dissolving the lyophilized silk fibroin in HFIP at room temperature. The viscosity and conductivity of the solutions were measured with a Couette viscometer (Bohlin V88) with a shear rate from 24.3 to 1216 per second, and a Cole-Parmer conductivity meter (19820) at room temperature, respectively.

Electrospinning

Electrospinning was performed with a steel capillary tube with a 1.0 mm inside diameter tip mounted on an adjustable, electrically insulated stand. The capillary tube was maintained at a high electric potential for electrospinning and mounted in the parallel plate geometry. The capillary tube was connected to a syringe filled with 10 ml of a silk/PEO blend or silk solution. A constant volume flow rate was maintained using a syringe pump, set to keep the solution at the tip of the tube without dripping. The electric potential, solution flow rate, and the distance between the capillary tip and the collection screen were adjusted so that a stable jet was obtained. By varying the distance between the capillary tip and the collection screen, either dry or wet fibers were collected on the screen.

Solution Treatment of Electrospun Mat from Silk/PEO Blend Solutions

Electrospun non-woven mats from silk/PEO blend solutions were immersed into a 90/10 (v/v) methanol/water solution for 10 min to induce an amorphous to β-sheet conformational transition of electrospun silk fiber and then washed with water for 24 hours at room temperature and 36.5° C., respectively, to remove PEO electrospun fiber from the mats.

SEM

Images of electrospun fibers were obtained with a LEO Gemini 982 Field Emission Gun SEM.

FT-IR

The infrared spectra were measured with a ATR-FTIR (Bruker Equinox 55) spectrophotometer. Each spectra for samples was acquired in transmittance mode on ZnSe ATR crystal cell by accumulation of 256 scans with a resolution of 4 cm$^{-1}$ and a spectral range of 4000-600 cm$^{-1}$.

XPS

A Surface Science Inc. Model SSX-100 X-ray photoelectron spectrometer was used to analyze the surface of the silk films to estimate the surface density of peptides. Survey scans (spot 1000 μm, resolution 4, window 1000 eV) were performed using a flood gun (charge neutralizer) setting of 5 eV and nickel wire mesh held over the sample to prevent charging of the sample surface.

Properties of Silk/PEO Blend Solutions with Pure Silk and PEO Solutions

Aqueous silk solutions without PEO did not electrospin; no fibers were formed because the viscosity and surface tension of the solution were not high enough to maintain a stable drop at the end of the capillary tip. Higher concentrations of silk in water to increase the viscosity of the solution resulted in gel formation. A stable drop at the end of the capillary tip was achieved once the PEO was added to the silk solution at the ratio shown in Table 1. The viscosity of pure silk solution was much lower than other solutions, even at a high concentration of 7.2% as shown in FIG. 1. A small portion of PEO in the silk solution increased the viscosity of the blends. The viscosities of silk/PEO blend solutions depended on the amount of PEO. The conductivities of silk and silk/PEO blend solutions were higher than pure PEO solutions at room temperature. All silk/PEO blend solutions showed good properties related to viscosity and conductivity in order to electrospin.

Fiber Formation and Morphology of Electrospun Silk/PEO from Water Solutions

The addition of PEO to silk solutions generated a viscosity and surface tension suitable for electrospinning. Aluminum foils was used as the collection screen. As the potential difference between the capillary tip and the aluminum foil counter electrode was gradually increased to 12 kV, the drop at the end of the capillary tip elongated from a hemispherical shape into a cone shape, often referred to as a Taylor cone. The applied 12 kV resulted in a jet being initiated near the end of the capillary tip. The distance between the tip and the collector was 200 mm and flow rate of all fluid was 0.02 ml/min to 0.05 ml/min. Before all solutions were electrospun, Teflon fluid was deposited on collection screen to peel off the mat easily.

The morphology and diameters of the electrospun fibers produced were examined using high resolution low voltage SEM. All silk/PEO blend solutions produced fine uniform fibers with less than 800 nm average fiber diameters (Table 1).

Figure 2:
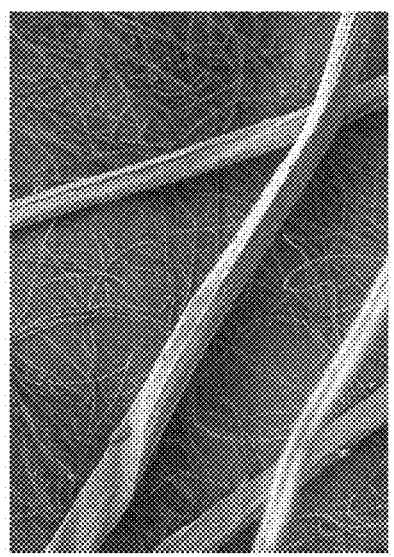
FIG. 2 is a scanning electron micrograph of electrospun fibers (No. 6) and sericin extracted *Bombyx mori* silk fiber (500 magnification).
Figure 3B:
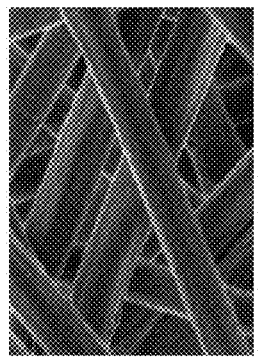
FIGS. 3A-3D are scanning electron micrographs of electrospun fibers (No. 1): (a) an elecrospun fiber, (b) after methanol treatment, (c) after dissolved in water at room temp and (d) after dissolved in water at 36.5° C.
Figure 3D:
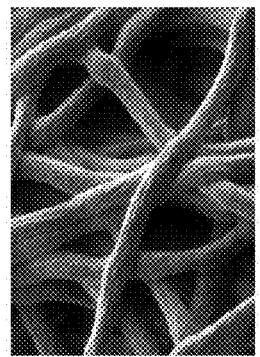
Figure 3A:
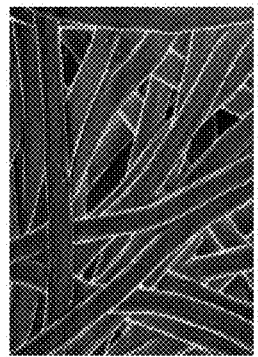
Figure 3C:
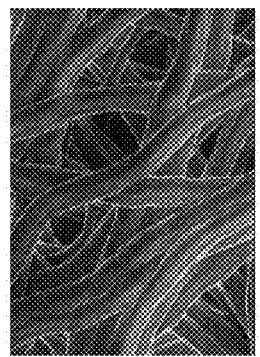

The fiber size was compared between sericin extracted silkworm silk and electrospun fibers (No. 6) (FIG. 2). The size of electrospun fiber was 40 times smaller than the native silk fiber. The individual electrospun fibers appeared to be randomly distributed in the non-woven mat. A micrograph of the electrospun fibers from a silk/PEO solution in water are shown in FIGS. 3A-3D.

XPS was used to estimate the surface composition of the mats. Table 2 shows the respective peak intensities of O1s, C1s or N1s of PEO, silk fibroin and silk/PEO blends from electrospun mats. The ratios of N1s/C1s and O1s/C1s of the silk mat were 0.31 and 0.40, respectively. In the case of the silk/PEO mats, N1s/C1s decreased to 0.16 at minimum and O1s/C1s increased to 0.49 at maximum. Based on these ratios we can estimate the fiber composition as shown in Table 2.

Solvent Treatment of Electrospun Mats

Figure 4:
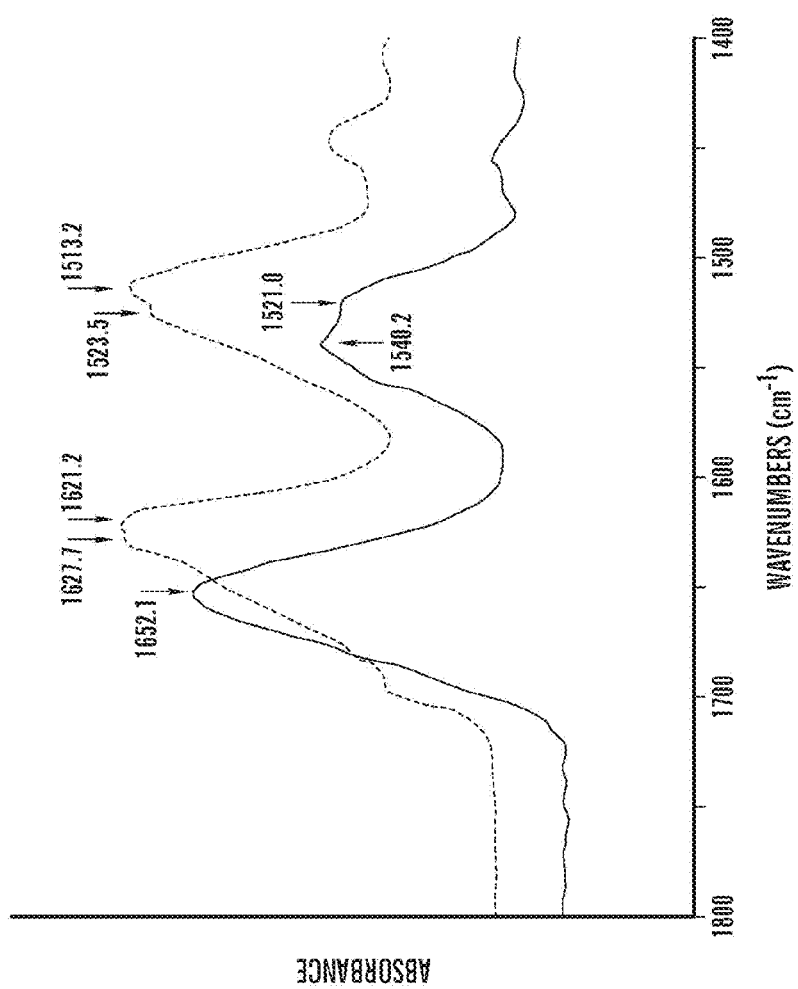
FIG. 4 is an ATR spectra of electrospun mat from silk/PEO blend solutions (No. 6) (dotted line: after methanol/water (90/10 v/v) treatment).

The mat was contacted with a 90/10 (v/v) methanol/water solution for 10 minutes to induce crystallization of silk and then stored in warm water at 36.5° C. for 24 hours to extract PEO. The structure change of silk fiber between just electrospun fiber and fiber after methanol treatment was observed by ATR-FTIR. As shown in FIG. 4, its structure was random coil or silk I, when it was just electrospun. So it was easily soluble in water and lost fiber structure quickly. But, after methanol treatment, its structure was changed into beta-sheet in FIG. 4. So, even after it was stored in water, it showed fine fiber structure.

XPS was used to analyze the surface of the mat after methanol/water treatment and washing with water to estimate the surface composition. Table 2 shows the XPS spectra results of PEO, silk fibroin and silk/PEO blend electrospun mats. Their respective peak intensities of O1s, C1s or N1s are also shown in Table 2. The ratio of N1s and C1s of all blend mat was less than the silk mat (0.33) even after washing with water. Therefore the individual silk/PEO electrospun fibers have PEO phases inside. Based on these ratios we can estimate the composition of the surface of the mat, relative of the solution used in spinning.

Example II

Materials

Cocoons of *B. mori* silkworm silk were obtained from M Tsukada, Institute of Sericulture, Tsukuba, Japan. PEO with an average molecular weight of 9×105 g/mol and polyethylene glycol (PEG) (3,400 g/mol) were purchased from Aldrich and used without further purification.

Preparation of Regenerated *B. mori* Silk Fibroin Solutions

*B. mori* silk fibroin solutions were prepared by modifying the procedure described earlier [25]. Cocoons were boiled for 30 min in an aqueous solution of 0.02 M Na2CO3, then rinsed thoroughly with water to extract the glue-like sericin proteins. The extracted silk was then dissolved in 9.3 M LiBr solution at room temperature yielding a 20 wt % solution. This solution was dialyzed in water using a Slide-a-Lyzer dialysis cassette (Pierce, MWCO 2000) for 48 hrs. The final concentration of aqueous silk solution was 7.0 to 8.0 wt %, which was determined by weighing the remaining solid after drying.

Preparation and Treatment of Blend Films

Various silk blends in water were prepared by adding 4 wt % PEG or PEO solutions into the silk aqueous solutions. The blending ratios (silk/PEG or PEO) were 100/0, 95/5, 90/10, 80/20, 70/30 and 60/40 (w/w). The solutions were mildly stirred for 15 min at room temperature and then cast on polystyrene Petri dish surfaces for 24 hrs at room temperature in a hood. The films then placed vacuum for another 24 hrs. Silk fibroin and blend films were immersed in a 90/10 (v/v) methanol/water solution for 30 min to induce an amorphous to β-sheet conformational transition of the silk fibroin. After crystallizing the silk and silk/PEG or PEO blends using methanol, their solubility in water, 17 MΩ at 37° C., was determined for 48 hrs. This solubility test was performed in shaking incubator and shaking speed was 200 rpm. It was expected that just PEG or PEO would dissolve. Solubility was calculated by weight balance between before and after PEG or PEO extraction.

Characterization

Fractured surfaces of silk and silk/PEG or PEO blend films were imaged using a LEO Gemini 982 Field Emission Gun SEM. A Surface Science Inc. Model SSX-100 X-ray photoelectron spectrometer was used to analyze the surface of the silk films to estimate the surface density of silk peptide versus PEO. Survey scans (spot 1000 µm, resolution 4, window 1000 eV) were performed using a flood gun (charge neutralizer) setting of 5 eV and nickel wire mesh held over the sample to prevent charging of the sample surface.

A differential scanning calorimeter, DSC (2920 Modulated DSC) from TA Instruments, was utilized to determine the thermal properties of the silk and blended films. Indium was used to calibrate temperature and the sample was sealed in aluminum pan. Each scans were performed −20° C. to 320° C. with a rate of 10° C./min. Sample were cooled to −100° C. at 20° C./min.

Contact Angle Analysis

The contact angle using Millipore purified water droplet, 17 MΩ, on the silk and blend films was measured to determine surface hydrophilicity. The water droplet, approximately 5 µl, was applied using a syringe and 22-gauge needle, and the static contact angle measured using a goniometer (Rame-Hart, Inc.). This analysis was performed after methanol treatment.

Mechanical Properties of Silk and Blend Films

The tensile properties of specimens (5×50×0.2 mm) were measured with a crosshead speed of 15 mm/min using Instron tensile tester at ambient condition. Gauge length was set 30 mm and initial load cell of 100 kgf was applied. The tensile strength per cross-sectional area (kg/mm2) and the ratio of the relative elongation to the initial film length at break (%) were determined from an observation of the stress-strain curves.

Blending Silk with PEG or PEO

PEG and PEO were selected for blending with silk to improve silk film properties with aqueous processability and biocompatibility as key criteria. PEG or PEO were studied for blending (with molecular weights of 3,400 and 900,000 g/mol, respectively). Silk/PEG or PEO films were first prepared to identify concentrations of the components useful in materials processing. The films were cast from water solutions onto polystyrene Petri dish in various ratios (Table 4) and dried overnight. In the case of silk and PEG (3,400 g/mol)

blends, the two components separated macroscopically into two phases during film formation throughout the range of compositions studied. Poorer quality films formed from all blend ratios except silk/PEG (98/2). Blends from silk/PEG were immersed in a 90/10 (v/v) methanol/water solution for 30 min to content the fibroin to the insoluble β-sheet structure. After this crystallization process, phase separation was more pronounced because the PEG phases became opaque while the silk phase was still transparent. Because the phase separation in the silk/PEG (60/40) blend was the most pronounced, further characterization was not considered on silk/PEG (60/40) blends. However, in the case of silk and PEO (900,000 g/mol) blends, no macroscopic phase separation occurred between two components throughout the range of components studied.

Aqueous Solubility of Blend Films

Figure 5A:
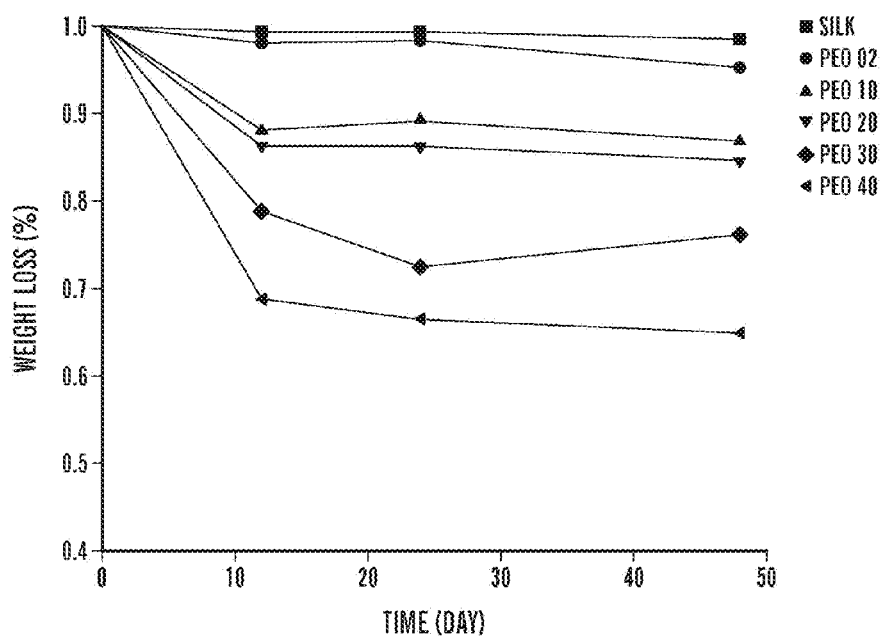
Figure 5B:
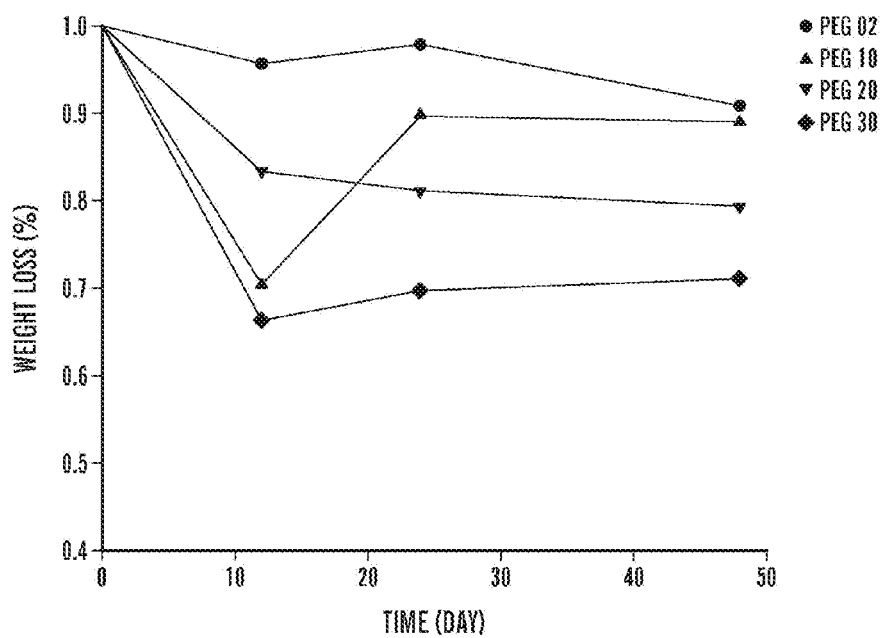

Solubility was calculated by weight balance between before and after PEO or PEG extraction, as shown in Table 5. Silk or blend films were separated into 6 parts, 3 parts of which were put into 3 independent glass vials for solubility testing at 12, 24 and 48 hrs. Up to 48 hrs, pure silk fibroin films did not show significant weight loss since they had been crystallized in methanol for 30 min before solubility testing. The slight weight change (~0.6%) during the test was believed to be due to the subtle effects of physical shear due to the vigorous shaking. Errors in the range of 1% were considered insignificant throughout the study. FIGS. 5A-5B showed the percentage weight loss of silk and silk/PEO or PEG blends according to time. In the case of silk/PEO blends, they showed relatively even weight loss throughout the range of compositions due to water solubility of PEO in the blends (FIG. 5A).

DSC

Figure 6:
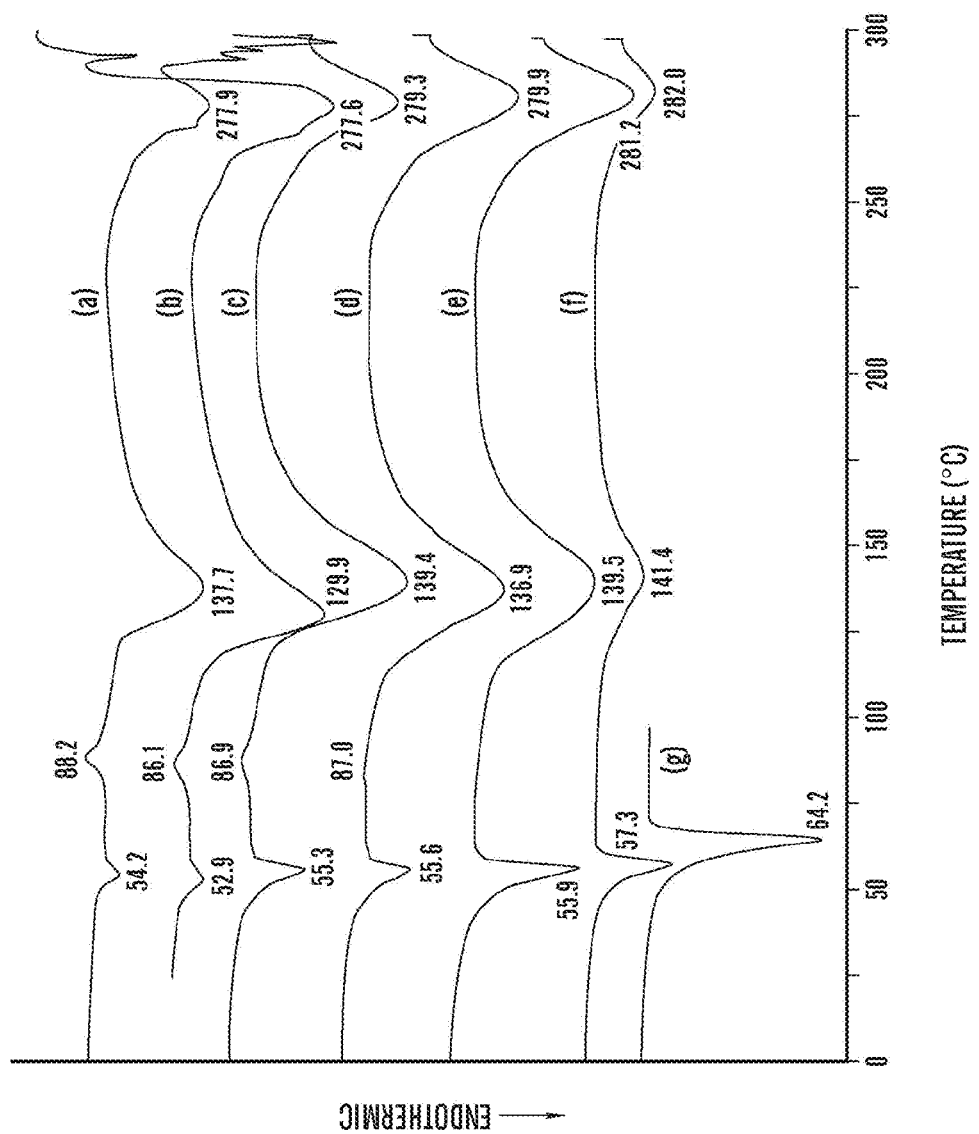
Figure 7:
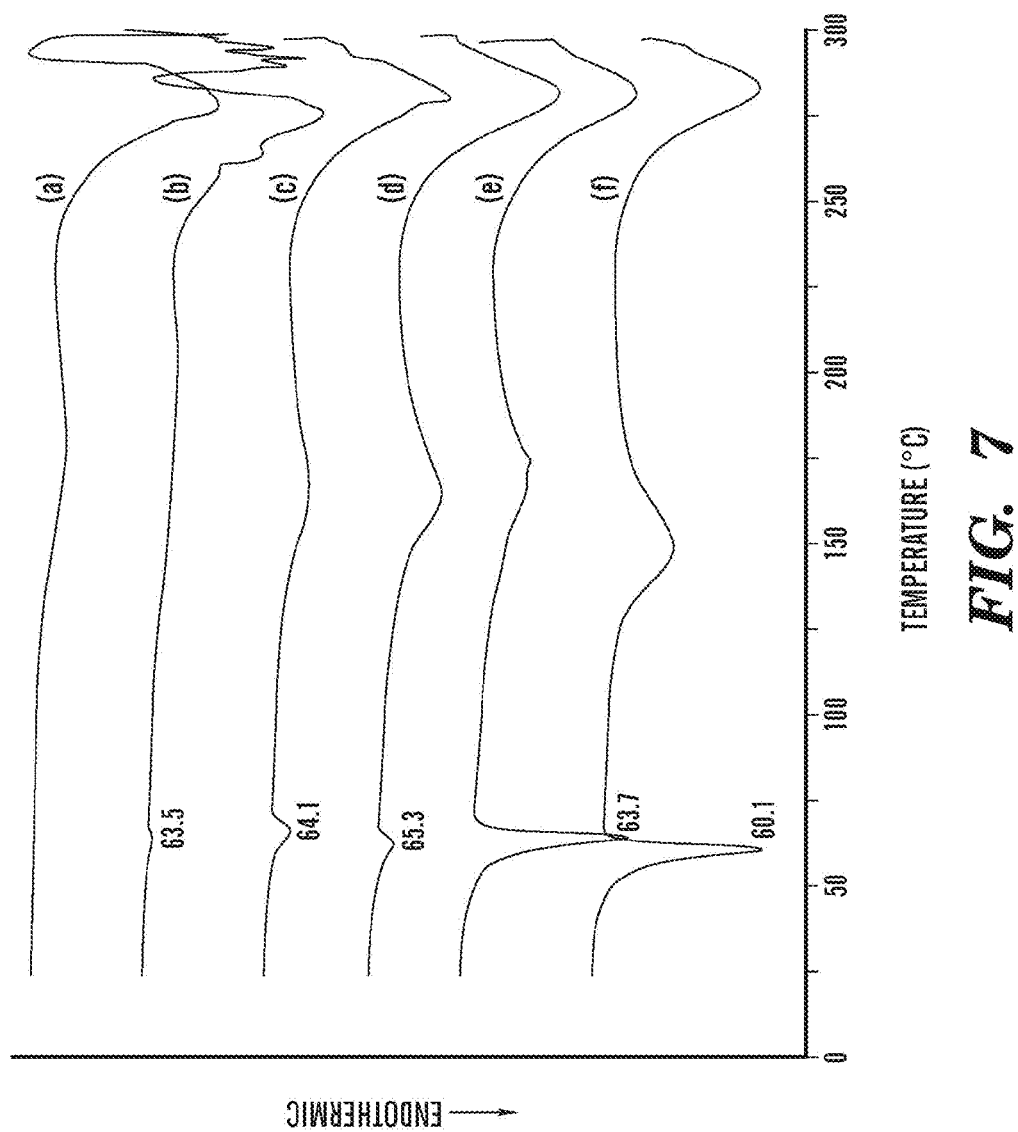

Thermal properties of silk and silk/PEO blends were observed by DSC before and after methanol treatment (FIGS. 6 and 7). DSC thermograms of the regenerated silk films are shown in FIG. 6(*a*) and FIG. 7(*a*), which are before and after methanol treatment, respectively. FIG. 6(*a*) shows an exothermic peak at about 88.2° C., attributed to the crystallization of silk fibroin induced by heat, and three endotherms at around 54.2, 137.7 and 277.9° C., attributed to the glass transition temperature, water evaporation and thermal degradation of silk fibroin, respectively [50]. On the other hand, FIG. 7(*a*) shows an endotherm at 278° C. without any trace of exothermic transition. This behavior is due to beta-sheet structure formation of silk film during methanol treatment [51].

In FIG. 6, overlapping of the characteristic thermal transitions of silk fibroin and PEO from 54.2 to 64.2° C. in blends seems the main feature emerging from the above DSC results. However, some changes appearing in the DSC pattern of blend films with high PEO content (more than 20 wt %) may suggest that a certain degree of interaction was established between silk fibroin and PEO. We mainly refer to the shift to lower temperature of the peak of PEO melting temperature and the disappearance of the crystallization peak of silk at 87 to 88° C., as well, with increasing PEO content in the blends. These effects can be interpreted as a decrease of PEO crystallization temperature in the blends and a prevention of the silk crystallization after PEO melts in the blends, due to the interaction of silk and PEO molecules. Otherwise, after methanol treatment of all samples, FIG. 7 shows the melting temperature of PEO in the blends shifted just slightly because of mostly the phase separation between silk and PEO domain by the crystallisation of silk. As it is shown in SEM observation as following, the two components formed micro phase separation in the blends.

Even though the maximum thermal degradation temperature seems to be less affected by methanol treatments and blending with PEO and its ratio, some changes were observed, such as a slight broadening of the decomposition endotherm with increasing the amount of PEO on the blend in the case of blends before methanol treatment.

XPS

XPS was used to estimate the surface composition of the films. Table 6 shows the respective peak intensities of O1s, C1s or N1s of silk fibroin and silk/PEO blend films before and after methanol treatments. The ratios of N1s/C1s were used to estimate the composition of silk and PEO before and after methanol treatments from the surface of films. Based on these ratios we can estimate the blend film composition as shown in Table 6. As the PEO portion was increased, the N1s/C1s of all blends was decreased in both of before and after methanol treatment. Especially, the N1s/C1s after methanol treatment on blend films was much lower than before methanol treatment. It could be estimated that the PEO part migrates into the surface of film by phase separation during methanol treatment, because of silk β-sheet formation. Since silk is relatively hydrophobic, it might be anticipated a lower content of silk on the film surface treated in methanol could be anticipated. However, the N1s/C1s ratio of silk/PEO (90/10) was increased after methanol treatment

SEM

The fractured cross section side and surface morphologies of the silk and silk/PEO or PEG blend films were examined using high resolution low voltage SEM after PEG or PEO extraction in warm water at 37 for 48 hrs. While the pure silk fibroin film exhibited a dense and uniform microstructure, the fractured surfaces of all silk/PEO blends showed a rough morphology due to the micro phase separation. The higher the PEO content in the films up to 40 wt %, the denser the film morphology based on cross sections. The silk/PEO (90/10) blend showed the least dense morphology from the fractured surfaces, which demonstrates that the PEO portion of the blend does not migrate to the surface during methanol treatment. This conclusion supports the SPS data. The silk/PEG blend films, unlike the silk PEO systems, did not show a different morphology than that seen with the pure silk fibroin films.

Contact Angle Measurements

The contact angle was measured on the silk and silk/PEO blend films after methanol treatment as shown in Table 7. The hydrophilicity of surface was increased with increasing the PEO ratio of the blend.

Mechanical Properties

The values of tensile modulus, rupture strength and elongation of silk and silk/PEO blend films are shown in Table 8. The pure silk film displayed the typical behavior of brittle materials. The addition of 2 wt % PEO to silk fibroin was effective in inducing a slight improvement of the mechanical properties of blend films. In other ratios of blend, tensile modulus and strength decreased with increasing the PEO content. However, elongation at break was increased slightly up to 10.9% in silk/PEO (60/40) blends. Methanol treatment of these samples did not significantly change the mechanical properties.

Drawing (Stretching) of Silk Blend Film

PEO02BM (silk/PEO 98/02 wt %) film blend sample was soaked in water for 5 minutes at room temperature and then stretched two times its original length. Then, the sample was dried at ambient conditions for 48 hrs followed by tensile testing on an Instron.

| Samples | Tensile Modulus (GPa) | Tensile Strength (MPa) | Elongation at Break (%) |
|---|---|---|---|
| PEO02BM[1] | 3.3 | 63 | 5.7 |
| PEO02ST[2] | 2.3 | 88 | 41 |

[1]BM: before methanol treatment,
[2]ST: stretched

Example III

Methods

Cocoons of *B. mori* silkworm silk were kindly supplied by M. Tsukada, Institute of Sericulture, Tsukuba, Japan. PEO with an average molecular weight of 9×105 g/mol (Aldrich) was used in the blends.

Preparation of Silk Matrices and Regenerated *B. Mori* Silk Fibroin Solutions

To prepare the silk matrices for cell seeding experiments, white Brazilian raw *Bombyx mori* silkworm fibers were extracted for 1 hour at 90° C. in an aqueous solution of 0.02 M Na2CO3 and 0.3% (w/v) detergent as previously described [33] to remove sericin, the antigenic glue-like proteins that encapsulate the fibroin fibers following secretion from the silkworm. A 3-cm long silk wire-rope matrices consisting of 540 silk fibers (pre-extraction) were generated for use in this study by crimping ends with stainless steel 316L collars (1 cm in length, 2.2 mm I.D, 3 mm O.D.).

Regenerated *B. mori* silk fibroin solutions was prepared as a modification of our earlier procedure. Cocoons were boiled for 30 mm in an aqueous solution of 0.02 M Na2CO3, and then rinsed thoroughly with water to extract sericin proteins [25]. The extracted silk was then dissolved in 9.3 M LiBr solution at 60° C. yielding a 20% (w/v) solution. This solution was dialyzed in water using a Slide-a-Lyzer dialysis cassette (Pierce, MWCO 3500). The final concentration of aqueous silk solution was 8.0 wt %, which was determined by weighing the remaining solid after drying.

Preparation of Spinning Solutions

Silk/PEO blends (80/20 wt/wt) in water were prepared by adding 5 ml of 5.0 wt % PEO (900,000 g/mol) into 20 ml of 8 wt % silk aqueous solution generating 7.5 wt % silk/PEO solutions. To avoid the premature formation of β-sheet structure during blending the two solutions, the solutions were stirred gently at low temperature, 4° C.

Electrospinning

Electrospinning was performed with a steel capillary tube with a 1.5 mm inside diameter tip mounted on an adjustable, electrically insulated stand as described earlier [9, 32]. The capillary tube was maintained at a high electric potential for electrospinning and mounted in the parallel plate geometry. The capillary tube was connected to a syringe filled with 10 ml of a silk/PEO blend solution. A constant volume flow rate was maintained using a syringe pump, set to keep the solution at the tip of the tube without dripping. The electric potential, solution flow rate, and the distance between the capillary tip and the collection screen were adjusted so that a stable jet was obtained. By varying the distance between the capillary tip and the collection screen, either dry or wet fibers were collected on the screen.

Treatment of Electrospun Mats

Electrospun non-woven mats from silk/PEO blend solutions were immersed into a 90/10 (v/v) methanol/water solution for 10 mm to induce an amorphous to silk β-sheet conformational transition, and then washed with water for 48 hours at 37° C. to remove PEO from the mats. This process was performed in a shaking incubator at 50 rpm. Two sets of electrospun mats were studied for cell interactions, with and without PEO present.

XPS

A Surface Science Inc. Model SSX-100 X-ray photoelectron spectrometer was used to analyze the surface of the silk films to estimate the surface density of silk versus PEO. Survey scans (spot 1000 μm, resolution 4, window 1000 eV) were performed using a flood gun (charge neutralizer) setting of 5 eV and nickel wire mesh held over the sample to prevent charging of the sample surface.

DSC

A differential scanning calorimeter (DSC) (2920 Modulated DSC) from TA Instruments was utilized to determine the thermal properties of the electrospun fibers. Indium was used to calibrate temperature and the sample was sealed in an aluminum pan. Each scan was performed between −20° C. to 100° C. with a rate of 10° C./mm.

Optical Polarizing Microscopy

A Zeiss Axioplan 2 with digital camera and Linkam. LTS 120 hot stage was used to observe the morphologies of the electrospun fiber. The images were taken and compared before heating the fiber at room temperature and after heating to 100° C. at a rate of 5° C.

Mechanical Properties of Electrospun Mats

The mechanical properties of specimens (8×40×0.5) (mm) were measured with a crosshead speed of 20 mm/mm using an Instron tensile tester at ambient condition. Gauge length was set at 20 mm and an load cell of 100 kg f was used. The tensile strength per cross-sectional area ($kg/mm^2$) and the ratio of the relative elongation to the initial film length at break (%) were determined from an observation of the stress-strain curves. All samples were stored in vacuum at room temperature before test. Each test was performed 5 times.

Cells and Matrix Seeding

BMSCs were isolated, cultured expanded and stored as previously described [33]. Briefly, human unprocessed whole bone marrow aspirates were obtained from donors <25 years of age (Clonetic-Poietics, Walkersville, Md.), resuspended in Dulbecco Modified Eagle Medium (DMEM) supplement with 10% fetal bovine serum (FBS), 0.1 mM nonessential amino acids, 100 U/ml penicillin and 100 mg/L streptomycin (P/S), and 1 ng/ml basic fibroblast growth factor (bFGF) and plated at 8 μl aspirate/cm2 in tissue culture polystyrene; non-adherent hematopoietic cells were removed with the culture medium during medium exchange after 4 days. Thereafter, medium was changed twice a week. Primary BMSCs were detached prior to confluency using 0.25% trypsin/1 mM EDTA and replated at 5×103 cells/cm2. First passage (P1) hBMSCs near confluency were trypsinized and frozen in 8% DMSO/IO % FBS/DMEM for future use.

Frozen P1 hBMSCs were defrosted and replated at $5×10^3$ cells/cm2 (P2), trypsinized when near confluency, and used for matrix seeding. Electrospun fibroin mats (1 cm×1 cm) were incubated with 70% alcohol for 30 minutes followed by an extensive washing procedure with sterile PBS before cell seeding. Matrices were seeded with cells (25000 cells/cm2) by direct pipetting of the cell suspension onto the silk matrices and incubated at 37° C./5% $CO_2$ in 2 ml of cell culture medium without bFGF for the duration of the experiment. The cell culture medium was changed every 4 days.

For seeding BMSCs to silk native fiber matrices, gas sterilized (ethylene oxide) silk matrices (3 cm in length) were placed in a custom designed Teflon seeding chamber to increase cell-matrix interaction. The chamber has twenty-four wells, each 3.2 mm wide by 8 mm deep by 40 mm long (1 ml total volume). Matrices were inoculated with 1 ml of cell suspension at a concentration of 2×106 cells/ml by direct pipetting, incubated for 2 hours at 37° C./5% $CO_2$ and transferred to tissue culture flasks for the duration of the experiment in an appropriate amount of cell culture medium without bFGF. Following seeding, the silk matrices were cultured in an appropriate amount of DMEM (10% FBS) for 1 day and 14 days.

Cell Proliferation Assays

Cell Counting

After 1, 7 and 14 days, the silk mats were harvested, washed with PBS to remove non-adherent cells, then incubated in 0.5 ml of 0.25% typsin/1 mM EDTA at 37° C. for 5 minutes. The trypsinization was stopped by adding 0.5 ml of culture medium containing 10% FBS to each sample. The cell numbers were then counted by using a hematocytometer and microscope.

MTT

Cell proliferation was measured by 3-[4,5-dimethylthiazol-2-yl]-2,5-diphenyl tetrazolium bromide (MTT) (Sigma, St. Louis, Mo.) staining. After 14 days, seeded silk matrices or silk mats were incubated in MIT solution (0.5 mg/ml, 37° C./5% CO2) for 2 hours. The intense red colored formazan derivatives formed was dissolved and the absorbance was measured with a microplate spectrophotometer (Spectra Max 250, Molecular Devices, Inc, Sunnyvale, Calif.) at 570 nm and the reference wavelength of 690 nm.

Scanning Electron Microscopy (SEM)

SEM was used to determine cell morphology seeded on the silk fibroin.

Following harvest, seeded silk matrices were immediately rinsed in 0.2 M sodium cacodylate buffer, fixed in Karnovsky fixative (2.5% glutaraldehyde in 0.1 M sodium cacodylate) overnight at 4° C. Fixed samples were dehydrated through exposure to a gradient of alcohol followed by Freon (1,1,2-trichlorotrifluoroethane, Aldrich, Milwaukee, USA) and allowed to air dry in a fume hood. Specimens were examined using LEO Gemini 982 Field Emission Gun SEM (high resolution low voltage SEM) and JEOL JSM-840A SEM.

Results and Discussion

Electrospinning of Silk/PEO Solutions

In order to increase the viscosity of aqueous silk solution (8 wt %), PEO (MW 900K) was added with the ratios of 4/1 (silk/PEO wt/wt) shown in Table 9 as described above and in our previous work [32]. The viscosity and surface tension of the pure silk solution (8 wt %) were not high enough to maintain a stable drop at the end of the capillary tip. The addition of PEO to silk solutions generated a viscosity and surface tension suitable for electrospinning. The distance between the tip and the collector was 21.5 cm and flow rate of the fluid was 0.03 ml/min. As the potential difference between the capillary tip and the aluminum foil counter electrode was gradually increased 12.5 kV (E=0.6 kV/cm), the drop at the end of the capillary tip elongated from a hemispherical shape into a cone shape. The morphology and diameters of the electrospun fibers were examined using SEM. Silk/PEO blend solution produced fine uniform fibers with 700 nm±50 average fiber diameters (Table 9). The individual electrospun fibers appeared to be randomly distributed in the non-woven mat.

Figure 8B:
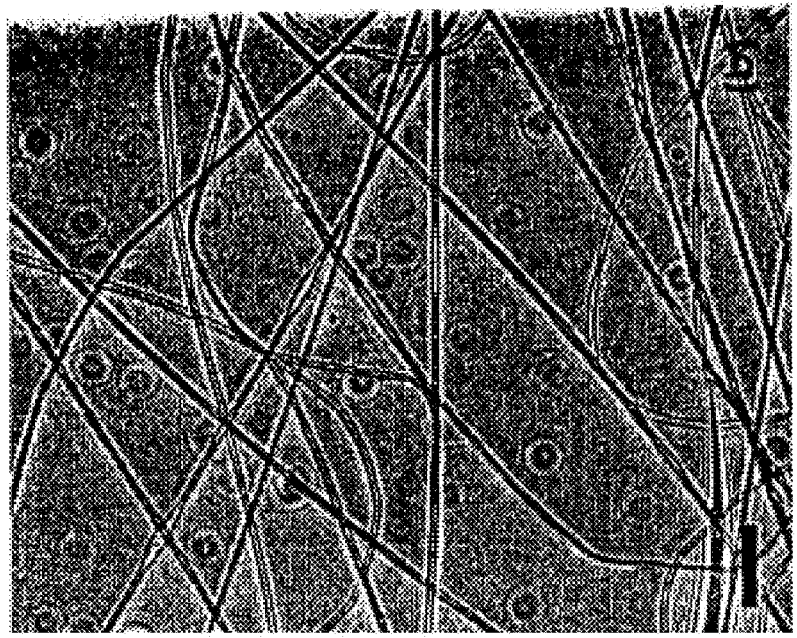
FIGS. 8A-8B show optical polarizing images of electrospun fibers (scale bar: 10 μM): (a) before heating at room temperature and (b) after heating up 100° C. at a rate of 5° C./min.
Figure 8A:
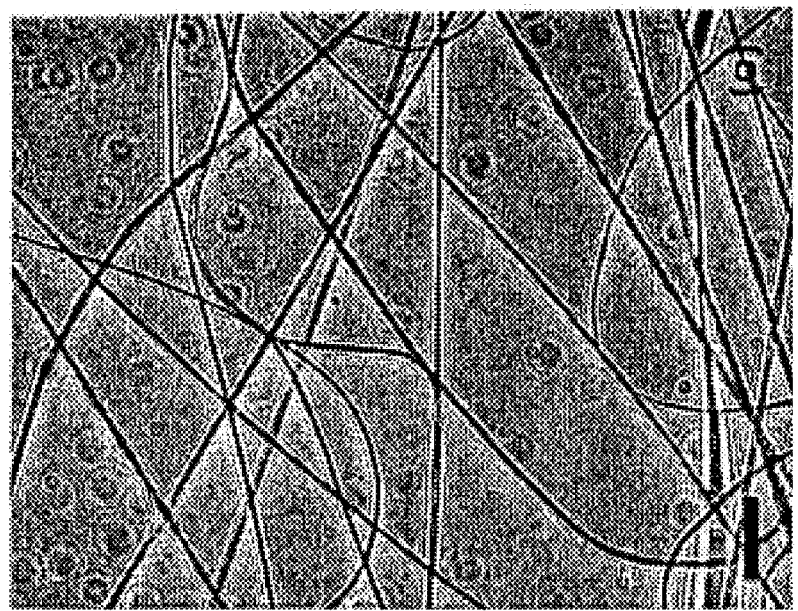

The electrospun fibers from the blend solution were observed by optical microscopy with a hot stage. The melting temperature of PEO is around 60° C. [78] and silk fibroins do not show any thermal transitions up to 100° C. [79]. FIG. 8(a) was taken at room temperature and FIG. 8(b) after heating to 100° C. at a rate of 5° C./min. This result confirms that both polymer (PEO and silk fibroin) were presenting single in the electrospun fibers. The fact that fibers remained intact in both temperatures shows that the melt out of PEO didn't have any effect on their morphology and structure. Therefore, the fiber integrity depends only on silk fibroin.

Figure 9:
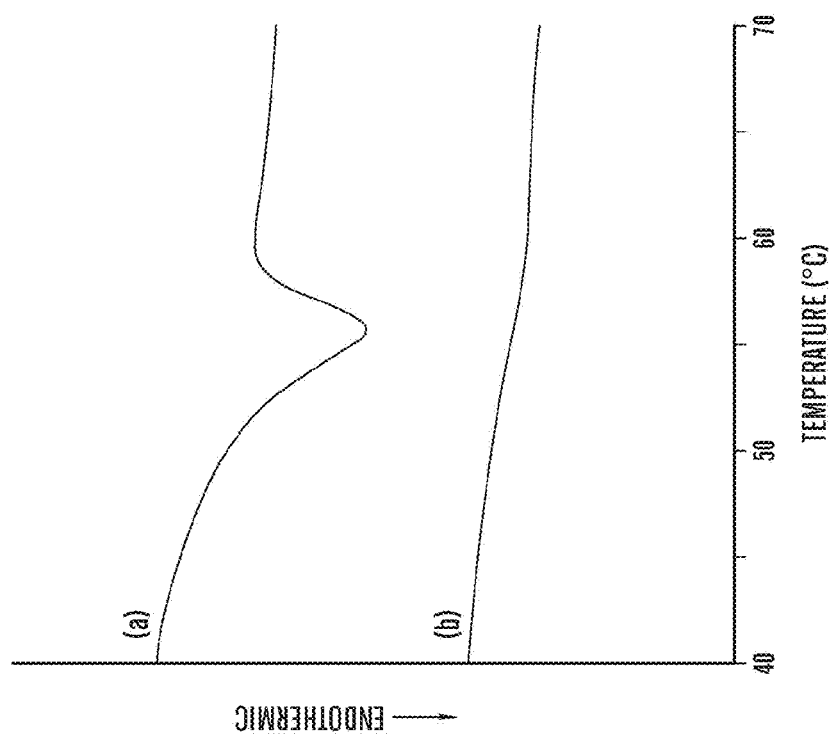
Figure 10C:
FIGS. 10A-10C show low voltage high resolution scanning electron micrographs of electrospun mats: (a) individual fiber surface after methanol treatment, (b) PEO non-extracted mat, and (c) PEO extracted mat.
Figure 10A:
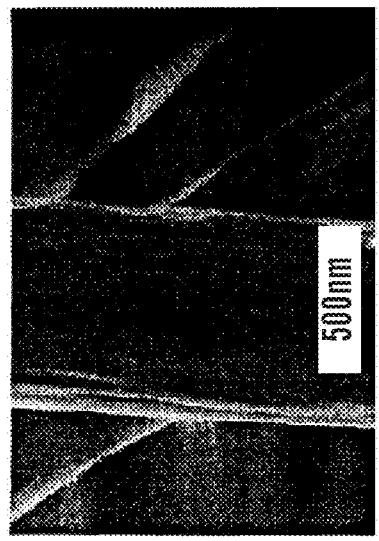
Figure 10B:
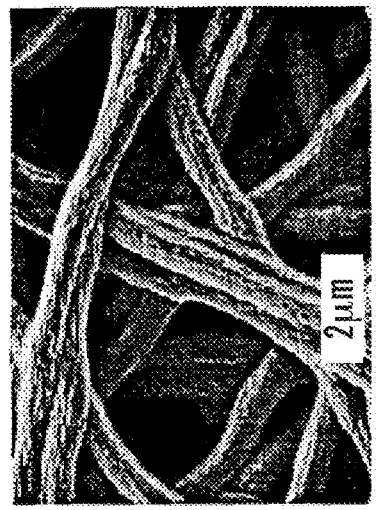

Electrospun mats were treated with methanol to eliminate solubility in water. The surface composition of the mats before and after methanol treatment was determined by XPS (Table 3). The respective peak intensities of O1S, C1S or N1S of two silk/PEO blends from electrospun mats are illustrated. The ratios of N1S/C1S of the mat was 0.23 before methanol treatment. After methanol treatment, the N1S/C1S increased to 0.28 (Table 3) as expected due to solubility of PEO in methanol. When PEO was extracted from the mat at 37° C. in water for 2 days, the N1S/C1S increased to 0.31, which did not change even after 7 days. Therefore, after the PEO extraction during 2 days, almost all the PEO had been extracted. DSC measurements confirmed the elimination of PEO by this treatment as well (FIG. 9). After methanol treatment, the electrospun mats showed a melting temperature peak for PEO around 56.5° C. (FIG. 9), after extraction in water the peak was absent. To observe delicate surface morphology of electrospun fiber, high resolution low voltage SEM was used without a conductive-coating on the sample. After methanol treatment, a surface morphology of electrospun mat was observed and each individual fiber showed the fibril structure with around 110 nm from its surface similar to degummed native silk fiber (FIG. 10(a)) [67]. Even after PEO extraction from the electrospun mats, surface morphology was maintained (FIGS. 10(b) and (c)). Two sets of electrospun mats with and without PEO present were compared with native silk fibro in fibers for cell interactions.

Figure 11:
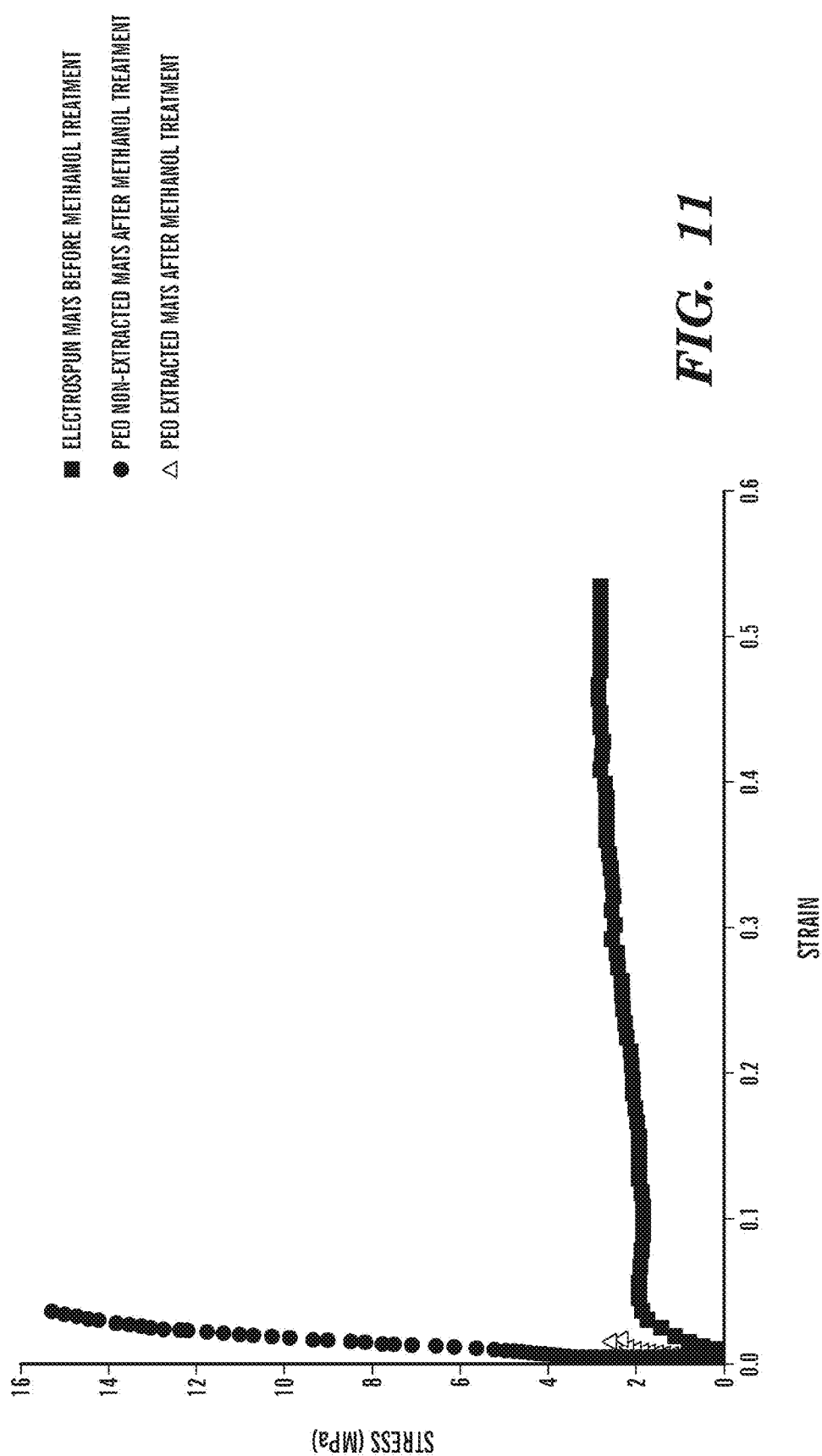

The values of tensile modulus, strength and elongation of electrospun mats are shown in FIG. 11. The scaffold structure must provide sufficient mechanical properties during the process of tissue regeneration. After methanol treatment of electrospun mats, its tensile modulus, tensile strength and elongation values were 624.9±0.9 MPa, 13.6±1.4 MPa and 4.0±2.0%, respectively. By β-sheet structure formation of electrospun silk fibroin during methanol treatment [32], its tensile modulus and strength was higher and elongation was lower than before methanol treatment. After PEO extraction from electrospun mats, its mechanical properties were largely decreased due to brittleness as shown in regenerated silk fibroin films [39]. The existence of PEO was effective in the improvement of the mechanical properties of electrospun mats. Even though its elongation was decreased after methanol treatment, toughness was much higher before PEO then after PEO extraction. Electrospun silk fibroin mats in this study were comparable with other biodegradable electrospun mats using PGA [80], PLGA [81], collagen [82], collagen/PEO blends [83] that were used as scaffolds for tissue regeneration.

Cell Culture Experiments

Figure 12:
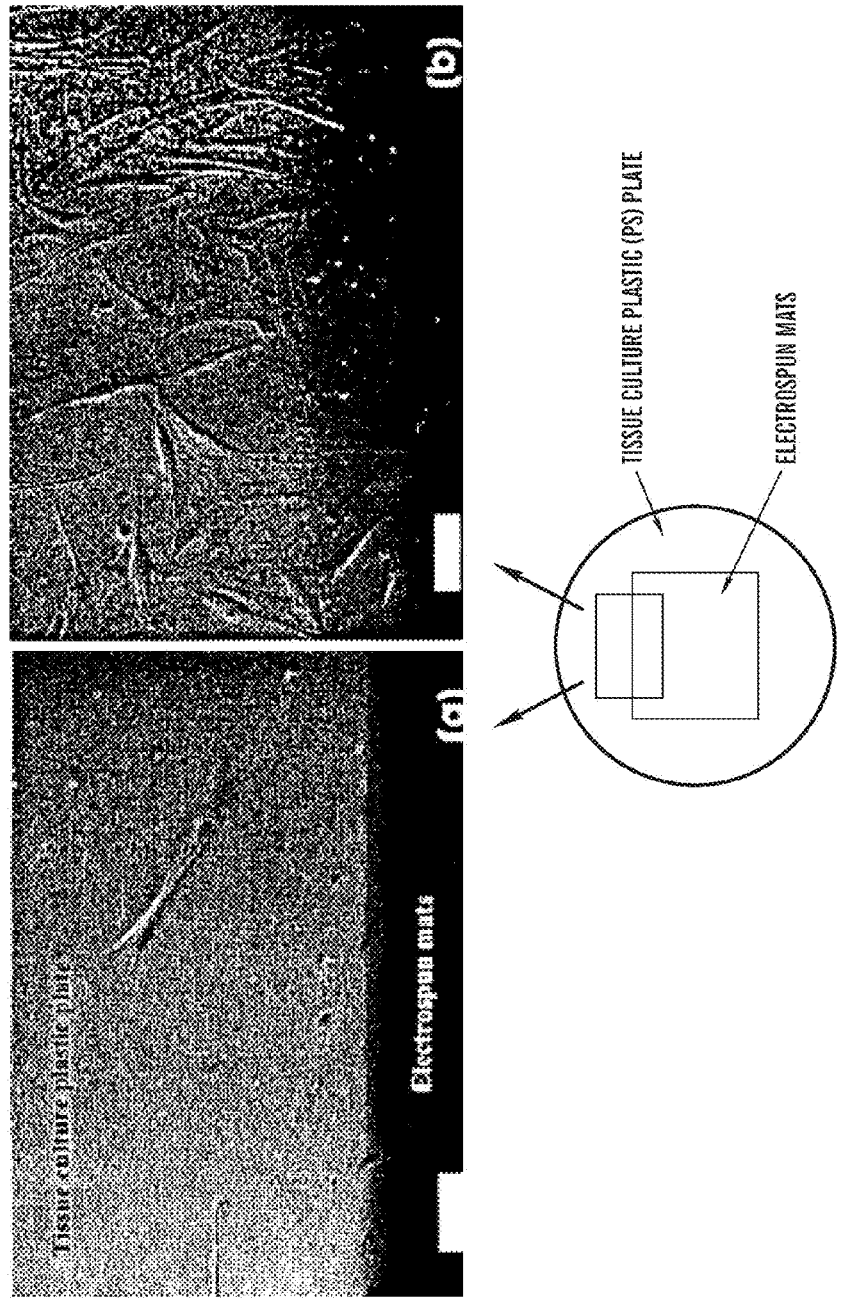
Figure 14A:
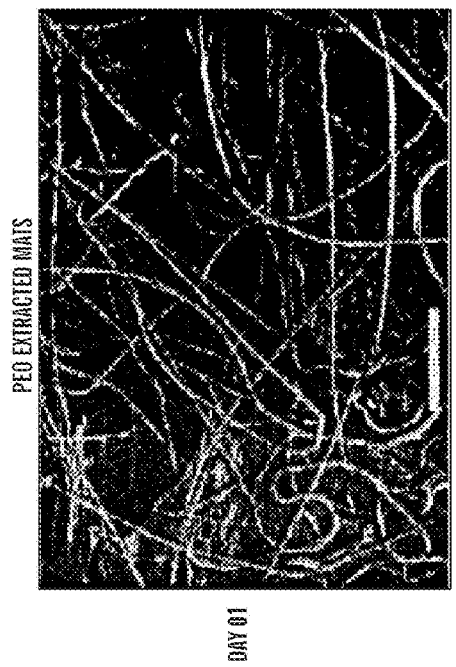
FIGS. 14A-14D show scanning electron micrographs of BMSCs growing on electrospun mats after 1 and 14 days: (scale bars: (a) 50 μm, (b) 20 μm, (c) 20 μm, and (d) 10 μm).
Figure 14B:
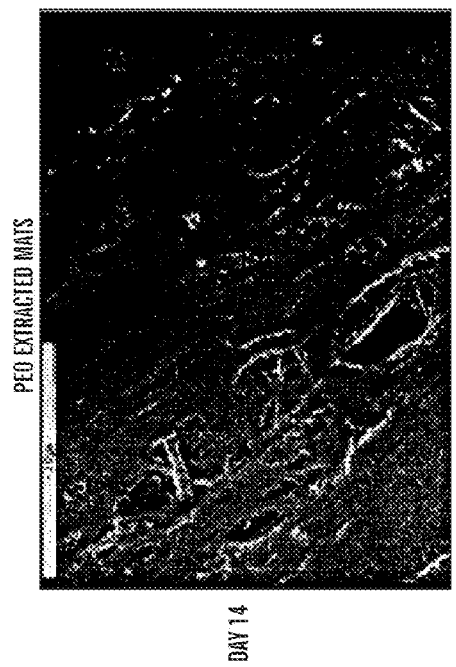
Figure 14C:
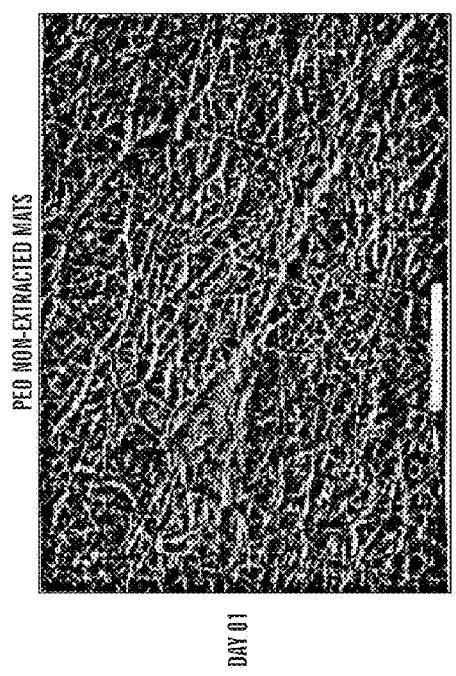
Figure 14D:
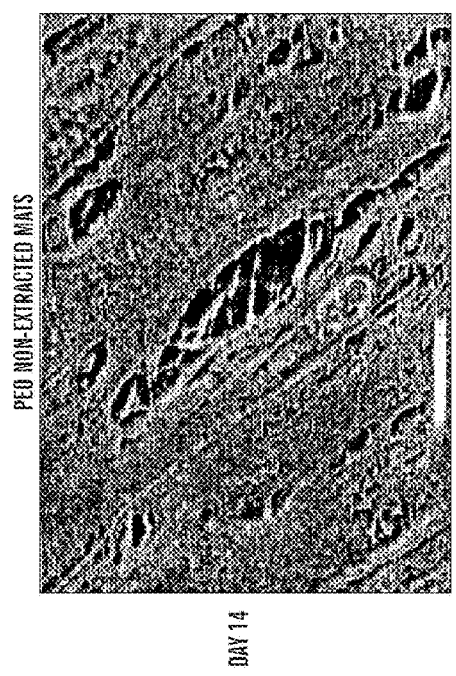

A tissue engineering scaffold material must support cellular attachment and growth. To evaluate cellular behavior on the electrospun fibroin, BMSCs were seeded and cultivated on the PEO non-extracted or extracted samples placed in Petri dishes. At 24 hours after seeding, it was observed that the PEO extracted silk mats were surrounded by cells growing on tissue culture plastic. In contrast, few cells were observed around the non-extracted mats (FIG. 12). This phenomenon may suggest that at day 1, PEO was released from the non-extracted silk mats which kept BMSC from attaching to the surrounding area. The cell number from day 1 showed that 50% more cells were attached to PEO-extracted silk mats when compared with non-extracted silk mats. BMSC attachment to silk mats was confirmed by SEM (FIG. 13). Cells were observed on both PEO extracted and non-extracted mats 1 day after cell seeding, but with a higher density on the PEO extracted samples which cope with the data from cell counting experiment. Presumably the soluble PEO released from the non-extracted mats during incubation kept the cells from attaching to the fibers, due to the hydrophilic nature of the PEO [84], which limits protein adsorption [85-87]. While the cells on non-extracted mats stayed on the surface of the material (FIG. 14(*a*)), some cells migrated underneath the silk fibers on PEO extracted mats (FIG. 14(*b*)). However, after 14 days, the cells grew among fibers and covered the majority of the surface on both of the extracted and non-extracted fibers (FIGS. 14(*c*) and (*d*)).

Figure 15:
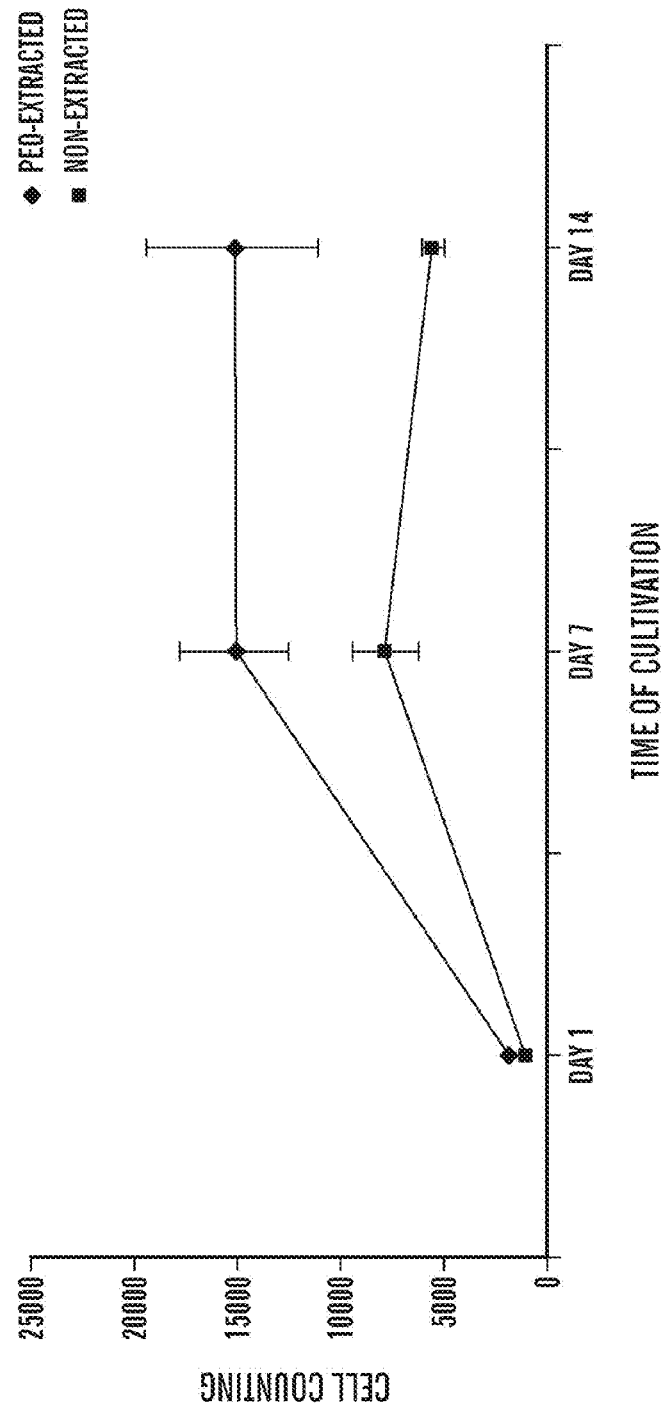
FIG. 15 shows proliferation of BMSCs seeded on electrospun mats (seeding density: 25,000 cells/cm$^2$, N=4). Error bars correspond to the standard deviations.
Figure 16:
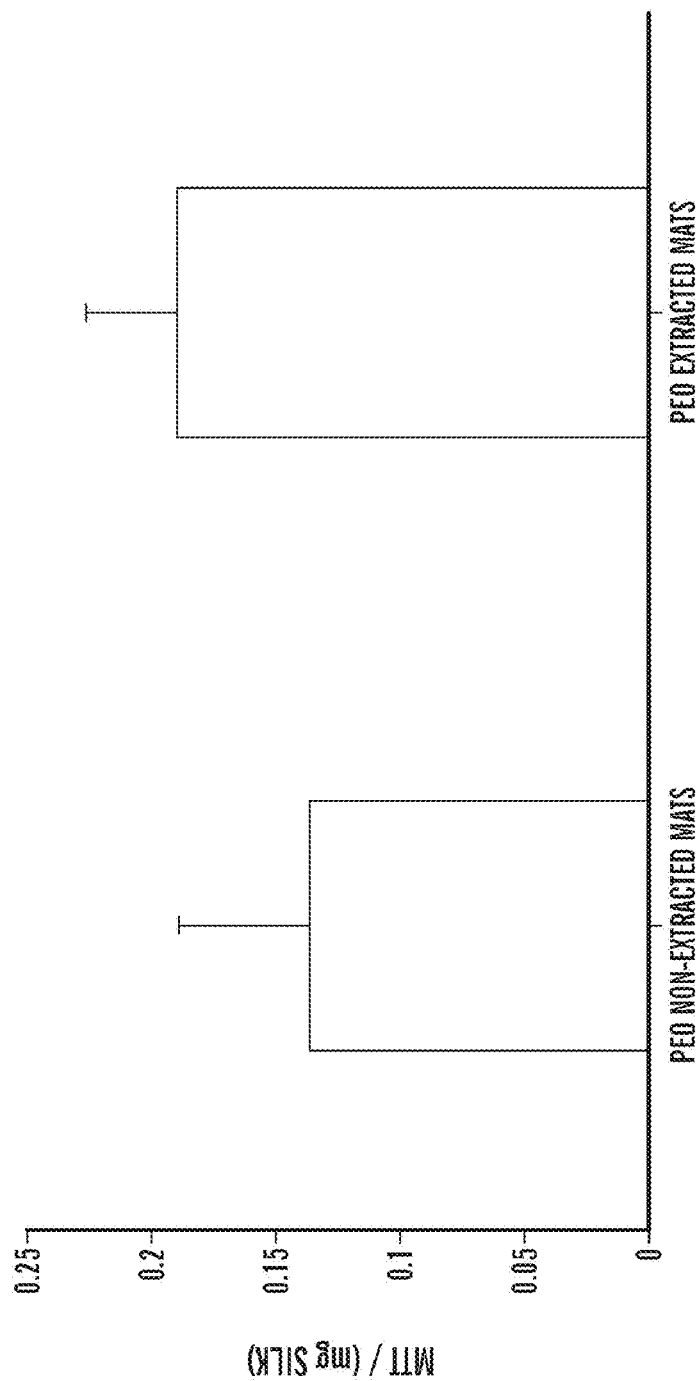
FIG. 16 shows MTT results with seeding conditions: 25000/cm$^2$, 20% serum after 14 days. Column heights correspond to the mean values and the error bars to the standard deviations (n=3).

In both extracted and non-extracted groups, the cell numbers were significantly increased ($p<0.01$) at day 7 when compared with day 1, which suggests cell growth (FIG. 15). Cell number on PEO extracted mats was significantly higher ($p<0.05$) by approximately 88% compared to the cell number on the non-extracted silk mats. Most parts of the PEO extracted and non-extracted mats were densely populated with BMSCs after 7 days of cultivation; a cell sheet and possible ECM covered the surfaces as determined by SEM (FIG. 13). This may explain the result that after day 7, the cell growth showed a plateau in both groups. The difference in cell density at day 7 and day 14 between the PEO-extracted and non-extracted groups may be due to differences in initial cell attachment caused by the existence of PEO. The presence of the PEO did not affect cell growth, which may be due to the fact that the PEO was extracted at 37° C. after a few days of incubation in cell culture medium. Our XPS results suggested that PEO was extracted after incubated the silk mats at 37° C. in water for 2 days (Table 3). Parallel seeding experiments were performed on native silk fibers. BMSCs were seeded on native silk matrices and cultured for 1 day or 14 days. SEM analysis showed that a few cells attached on native silk fibers (which have a diameter of ~15 µm on average) at day 1 (FIG. 13). BMSCs reached confluency and appeared to fully cover the silk matrices after 14 days of cultivation. BMSCs seeded and cultivated on the PEO extracted mats were present at higher densities compared to cells on the non-extracted mats. However, these differences were not significant ($p>0.05$) (FIG. 16).

Conclusions

Fine fiber mats with fibroin diameter 700±50 nm were formed from aqueous *B. mori* fibroin by electrospinning with PEO with molecular weight of 900,000. PEO supplied good mechanical properties to the electrospun mats, even though, initially, residual PEO inhibited cell adhesion. Within 1~2 days following PEO extraction, those effects were abolished and proliferation commenced. After 14 days of incubation, the electrospun silk mats supported extensive BMSC proliferation and matrix coverage. The ability of electrospun silk matrices to support BMSC attachment, spreading and growth in vitro, combined with a biocompatibility and biodegradable properties of the silk protein matrix, suggest potential use of these biomaterial matrices as scaffolds for tissue engineering.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

REFERENCES

The references cited below and incorporated throughout the application are incorporated herein by reference.

1. Doshi, J.; Reneker, D. H. Electrospinning Process and Applications of Electrospun Fibers. J. Electrostat. 1995, 35, 151-160.
2. Bognitzki, M.; Czado, W.; Frese, T.; Schaper, A.; Hellwig, M.; Steinhart, M.; Greiner, A.; Wendorff, J. H. Nanostructured fibers via electrospinning. Advanced Materials 2001, 13, 70-72.
3. Stitzel, J. D.; Pawlowski, K. J.; Bowlin, G. L.; Wnek, G. E.; Simpson, D. G.; Bowan, G. L. Arterial smooth muscle cell proliferation on a novel biomimicking, biodegradable vascular graft scaffold. Journal of Biomaterials Applications 2001, 16, 22-33.
4. Boland, E. D.; Bowlin, G. L.; Simpson D. G.; Wnek, G. E. Electrospinning of tissue engineering scaffolds. Polymeric Materials: Science & Engineering 2001, 85, 51-52.
5. Yarin, A. L.; Koombhongse, S.; Reneker, D. H. Bending instability in electrospinning of nanofibers. Journal of Applied Physics 2001, 89, 3018-3026.
6. Hohman, M. M.; Shin M.; Rutledge G.; Brenner M. P. Electrospinning and electrically forced jets. I. Stability theory. Physics of Fluids 2001, 13, 2201-2220.
7. Reneker, D. H.; Yarin, A. L.; Fong, H.; Koombhongse, S. Bending instability of electrically charged liquid jets of polymer solutions in electrospinning. Journal of Applied Physics 2000, 87, 4531-4547.
8. Shin Y. M.; Hohman M. M.; Brenner M. P.; Rutledge G. C. Electrospinning: A whipping fluid jet generates submicron polymer fibers. Applied Physics Letters 2001, 78, 1149-1151.
9. Shin, Y. M.; Hohman, M. M.; Brenner M. P.; Rutledge G. C. Experimental Characterization of Electrospinning: the Electrically Forced Jet and Instabilities. Polymer 2001, 42 9955-9967.
10. Fong H.; Chun I.; Reneker D. H. Beaded nanofibers formed during electrospinning. Polymer 1999, 40, 4585-4592.
11. Jaeger R.; Schönherr, H.; Vancso, G. J. Chain packing in electro-spun poly(ethylene oxide) visualized by atomic force microscopy. Macromolecules 1996, 29, 7634-7636.
12. Deitzel J. M.; Kleinmeyer, J. D.; Hirvonen J. K.; Tan N. C. B. Controlled deposition of electrospun poly(ethylene oxide) fibers. Polymer 2001, 42, 8163-8170.
13. Deitzel J. M.; Kleinmeyer J.; Harris D.; Tan N. C. B. The effect of processing variables on the morphology of electrospun nanofibers and textiles. Polymer 2001, 42, 261-272.
14. Bunning, T. J.; Jiang, H.; Adams, W. W.; Crane, R. L.; Farmer, B.; Kaplan, D.; Application of Silk. In Silk Polymers; Material Science and Biotechnology; Kaplan D. L., Adams W. W., Farmer B., Viney C., Eds.; ACS Symposium Series 544, Charlottesville, Va., 1993; pp 351-358.
15. Martin, D. C.; Tao, J.; Buchko, C. J. Processing and Characterization of Protein Polymers. In Protein-Based Materials; McGrath, K., Kaplan, D., Eds.; Birkhauser: Boston, Mass., 1997; pp 339-370.
16. Hudson, S. M. The Spinning of Silk-like Proteins into Fibers. In Protein-Based Materials; McGrath, K., Kaplan, D., Eds.; Birkhauser: Boston, Mass., 1997; pp 313-337.
17. Huang, L.; McMillan, R. A.; Apkarian, R. P.; Pourdeyhimi, B; Conticello, V. P.; Chaikof, E. L. Generation of synthetic elastin-mimetic small diameter fibers and fiber networks. Macromolecules 2000, 33, 2989-2997.

18. Anderson, J. P.; Nilsson, S. C.; Rajachar, R. M.; Logan, R.; Weissman, N. A.; Martin, D. C. Biomolecular materials by design. In Bioactive Silk-like Protein Polymer Films on Silicon Devices; Alper, M., Bayby, H., Kaplan, D., Navia, M., Eds.; Materials Research Society: Pittsburgh, Pa., 1994; Vol. 330, pp 171-177.
19. Buchko C. J.; Chen L. C.; Shen Y.; Martin D. C. Processing and microstructural characterization of porous biocompatible protein polymer thin films. Polymer 1999, 40, 7397-7407.
20. Buchko, C. J.; Kozloff K. M.; Martin D. C. Surface characterization of porous, biocompatible protein polymer thin films Biomaterials 2001, 22, 1289-1300.
21. Zarkoob, S.; Reneker, D. H.; Eby, R. K.; Hudson, S. D.; Ertley, D.; Adams, W. W. Generation of synthetic elastin-mimetic small diameter fibers and fiber networks. Polym. Prepr. (Am. Chem. Soc., Div. Polym. Chem.) 1998, 39, 244-245.
22. Asakura T.; Kaplan D. L. Silk Production and Processing. In Encyclopedia of Agricultural Science, Arntzen, C. J., Ritter, E. M. Eds.; Academic Press: New York, N.Y., 1994; Vol. 4, pp 1-11.
23. Kaplan, D. L.; Mello, C. M.; Arcidiacono, S.; Fossey, S.; Senecal, K.; Muller, W. Silk. In Protein-Based Materials, McGrath K., Kaplan D., Eds.; Birkhauser, Boston, Mass., 1997; pp 103-131.
24. Kim, S. W. Nonthrombogenic Treatments and Strategies. In Biomaterials Science: An introduction to Materials in Medicine, Ratner, B. D., Hoffman A. S., Schoen F. J., Lemons J. E., Eds.; Academic Press, New York, N.Y.; pp 297-308.
25. Sofia, S.; McCarthy, M. B.; Gronowicz G.; Kaplan, D. L. Functionalized silk-based biomaterials for bone formation. Journal of Biomedical Materials Research 2001, 54, 139-148.
26. Freddi, G.; Tsukada, M.; Beretta, S. Structure and Physical Properties of silk fibroin/polyacrylamide blend films. J. Appl. Polym. Sci. 1999, 71, 1563-1571.
27. Liang C. X.; Hrabayashi, K. Improvement of the physical properties of fibroin membrane with sodium alginate. J. Appl. Polym. Sci. 1992, 45, 1937-1943.
28. Freddi, G.; Romano, M.; Massafra M. R.; Tsukada M. Silk fibroin/cellulose blend films: preparation, structure, and physical properties. J. Appl. Polym. Sci. 1995, 56, 1537-1545.
29. Chen, X.; Li, W.; Yu, T. Conformation transition of silk fibroin induced by blending chitosan. J. Polym. Sci. B: Polym. Phys. 1997, 35, 2293-2296.
30. Tanaka, T.; Suzuki, M.; Kuranuki, N.; Tanigami, T.; Yamaura, K. Properties of silk fibroin/poly(vinyl alcohol) blend solutions and peculiar structure found in heterogeneous blend films. Polymer International 1997, 42, 107-111.
31. Sun, Y.; Shao, Z.; Ma, M.; Hu, P.; Liu, Y.; Yu, T. Acrylic Polymer-Silk Fibroin Blend Fibers. J Appl Polym Sci 1997, 65, 959-966.
32. H.-J. Jin, S. V. Fridrikh, G. C. Rutledge, and D. L. Kaplan, Biomacromolecules 3, 1233 (2002).
33. G. H. Altman, R. L. Horan, H. H. Lu, J. Moreau, L. Martin, J. C. Richmond, and D. L. Kaplan, Biomaterials 23, 4131 (2002).
34. Y. M. Shin, M. M. Hohman, M. P. Brenner, and G. C. Rutledge, Polymer 42, 9955 (2001).
35. Yang, G., Zhang, L., Liu, Y. Journal of Membrane Science 177, 153-161 (2000).
36. Chen, X., Li, W., Shao, Z., Thong, W., Yu, T., Journal of Applied Polymer Science 73, 975-980 (1999).
37. Chen, X., Li, W., Thong, W., Lu, Y., Yu, T., Journal of Applied Polymer Science 65, 2257-62 (1997).
38. Tanaka, T., Tanigami, T., Yamaura, K., Polymer International 45, 175-184 (1998).
39. Yamamura, K., Kuranuki, N., Suzuki, M., Tanigami, T., Matsuzawa, S., Journal of Applied Polymer Science 41, 2409-2425 (1990).
40. Demura, M., Asakura, T., Journal of Membrane Science 59, 39-52 (1991).
41. Kweon, H. Y., Park, S. H., Yeo, Y. W., Lee, Y. W., Cho, C. S. Journal of Applied Polymer Science 80, 1848-53 (2001).
42. Kesencl, K., Motta., A., Fambri, L., Migliaresi, C., Journal of Biomaterial Science Polymer Edition 12, 337-351 (2001).
43. Lee, K. Y., Fibers and Polymers 2, 71-74 (2001).
44. Alcantar, N. A., Aydil, E. S., Israelachvili, J. N., Journal of Biomedical Materials Research 51, 343-51 (2000).
45. Griffith, L. G. Acta Materialia 48, 263-277 (2000).
46. Ishida, M., Asakura, T., Yokoi, M., Saito, H., Macromolecules 23, 84-94 (1990).
47. Yoshimizu, H., Asakura, T., Journal of Applied Polymer Science 40, 1745-56 (1990).
48. Kiyotsukuri, T., Masuda, T., Tsutsumi, N., Sakai, W., Polymer 36, 2629-35 (1995).
49. Kaito, A., Kyotani, H., Tanaigaki, N., Wada, M., Yoshida, M., Polymer 41, 6395-6402 (2000).
50. Agarwal, N., Hoagland, D. A., Farris, R. J., Journal of Applied Polymer Science 63, 401-410 (1997).
51. Magoshi, J., Magoshi, Y., Nakamura, S., Applied Polymer Symposia 41, 187-204 (1985).
52. Zhou, C. Z., Confalonieri, F., Medina, N., Zivanovic, Y., Esnault, C., Yang, T., Jacquet, M., Janin, J., Duguet, M., Perasso, R., and Li, Z. G., Nucleic Acids Research 28, 2413-19 (2000).
53. Malstom, M., and Lindman, B., Macromolecules 25, 5440-45 (1992).
54. Yamada, H., Nakao, H., Takasu, Y., Tsubouchi, K., Material Science and Engineering 14, 41-46 (2001).
55. Jin, Fridrikh, S. V., Rutledge, G. C., Kaplan, D. L., Biomacromolecules 3, 1233-39 (2002).
56. Roseman, M. A., J. Molecular Biology 200, 513-22 (1988).
57. Ochi, A., Hossain, K. S., Magoshi, J., Nemoto, N., Biomacromolecules 3, 1187-96 (2002).
58. Discher, D. E., Eisenberg, A., Science 297, 967-973 (2002).
59. Kwon, K. W., Park, M. J., Bae, Y. H., Kim, H. D., Char, K., Polymer 43, 3353-58 (2002).
60. Vollrath, F., Knight, D. P., Nature 410, 541-548 (2001).
61. Magoshi, J., Mizuide, M., Magoshi, Y., J. Polymer Science: Polymer Physics Edition 17, 515-20 (1979).
62. Seidel, A., Liivak, O., Calve, S., Adaska, J., Ji, G., Yang, Z., Grubb, D., Zax, D. B., Jelinski, L. W., Macromolecules 33, 775-80 (2000).
63. Valluzzi, R., Szela, S., Avtges, P., Kirschner, D., Kaplan, D. L., J. Phys. Chem. B. 103, 11382-92 (1999).
64. Wilson, D., Valluzzi, R., Kaplan D., Biophysical Journal 78, 2690-2701 (2001).
65. Shen, Y., Johnson, M. A., and Martin, D. C., Macromolecules 31, 8857-64 (1998).
66. Asakura, T., Kuzuhara, A., Tabeta, R., Saito, H., Macromolecules 18, 1841-45 (1985).
67. Putthanarat, S., Stribeck, N., Fossey, S. A., Eby, R. K., Adams, W. W. Polymer 41, 7735-47 (2000).
68. van Beek, J. D., Hess, S., Vollrath, F., Meier, B. H., Proc. National Acad. Sciences 99, 10266-71 (2002).

69. Altman, G. H., Horan, R. L., Lu, H. H., Moreau, J., Martin, L, Richmond, J. C., Kaplan, D. L., Biomaterials 23, 4131-41 (2002).
70. Perez-Rigueiro, J., Viney, C., Llorca, J., Elices, M., J. Appl. Polym. Sci. 70, 2439-47 (1998).
71. Auvray, X., Perche, T., et al., Langmuir 8(11), 2671-79 (1992).
72. Lele, A. K., Joshi, Y. M., et al., Chemical Eng. Sci. 56 (20), 5793-5800 (2001).
73. Knight, D. P., Vollrath, F., Phil. Trans. R. Soc. Lond. B 357, 155-63 (2002).
74. Knight, D. P., Vollrath, F., Proc. Royal Soc. London Series B-Biol. Sci. 266(1418), 519-23 (1999).
75. Viney, C., Supramolecular Sci. 4(1-2), 75-81 (1997).
76. Minoura, N., Tsukada, M., Nagura, M., Biomaterials 11, 430-34 (1990).
77. Altman, G. H., Diaz, F., Jakuba, C., Calabro, T., Horan, R. L., Chen, J., Lu, H., Richmond, J., Kaplan, D. L., Biomaterials 24, 401-16 (2003).
78. Tsou, L., Sauer, J. A., Hara, M., J. Polymer Science B: Polymer Physics 38, 1369-76 (2000).
79. Magoshi, J., Nakamura, S., J. Applied Polymer Science 19, 1013-15 (1975).
80. Boland, E. D., et al., J. Macromol. Sci.-Pure Appl. Chem. A38, 1231-43 (2001).
81. Li, W. J., et al., J. Biomedical Materials Research 60, 613-21 (2002).
82. Matthews, J. A., et al., Biomacromolecules 3, 232-38 (2002).
83. Huang, L., et al., Polymer Edition 12, 979-93 (2001).
84. Neff, J. A., et al., J. Biomed. Mater. Res. 40, 511-19 (1998).
85. Elbert, D. L., Hubbell, J. A., Annual Review of Materials Science 26, 365-94 (1996).
86. Desai, N. P., Hubbell, J. A., Biomaterials 12, 144-53, (1991).
87. Park, H., Park, K., Pharmaceutical Research 13, 1770-76 (1996).
88. Nam, J., Young, P., Morphology of regenerated silkfibroin: effects of freezing temperature, alcohol addition, and molecular weight, Journal of Applied Polymer Science, Vol. 81, 3008-30021, (2001).
89. Ishaug, S., Crane, G., Miller M., Yasko, A., Yasmeski, M., Mikos, A., Bone Formation by three dimensional stromal osteoblast culture in biodegradable polymer scaffolds, Journal of Biomedical Materials Research, Vol. 36, 17-28, (1997).
90. Ishaug-Riley, S., Crane-Kruger, G., Yasmeski, M., Mikos, A., Three Dimensional culture of rat calvarial osteoblasts in porous biodegradable polymers, Biomaterials, Vol 19, 1405-1412, (1998).
91. Mingzhong L.; Zhengyu W.; Changsheng Z.; Shenzhou L.; Haojing Y; Dong H.; Hulan Y. study on Porous silk Fibroin Materials ii. Preparation and Characteristic of spongy Porous Silk Fibroin Materials. Journal of Applied Polymer Science 2001, 79, 2192-2199.
92. Agrawal M.; Ray R. Biodegradable polymeric scaffolds for musculoskeletal tissue engineering. Journal of Biomedical Material resources 2001, 55, 141-150.
93. Harris L.; Kim B.; Mooney D.; Open pore biodegradable matrices formed with gas foaming. Journal of Biomedical Material Research 1998, 42, 396-402.
94. Hutmacher D. Scaffolds in tissue engineering bone and cartilage. Biomaterials 2000. 21, 2529-2543.
95. Hutmacher D. Scaffold design and fabrication technologies for engineering tissues—state of the art and future perspectives. Journal of biomaterial science polymer science Edn 2001. 12, 107-124.

TABLE 1

Concentrations and Conductivities of Silk, PEO, Silk/PEO Blends and their Electrospun Fibers

| | Initial Conc. of Silk Solutions (%) | PEO Ratio to Silk (PEO/Silk) | Total Conc. (%) | Conductivity (μS) | Average Fiber Diam. |
|---|---|---|---|---|---|
| Silk | 7.2 | — | 7.2 | 240.0 | — |
| No 1 | 7.2 | 1/3 | 8.8 | 216.5 | 800 |
| No 2 | 7.2 | 1/4 | 8.3 | 191.9 | 600 |
| No 3 | 6.3 | 1/4 | 7.3 | 185.0 | 600 |
| No 5 | 6.0 | 1/3 | 7.4 | 209.0 | 800 |
| No 6 | 5.3 | 1/3 | 6.6 | 182.2 | 600 |
| No 7 | 4.1 | 1/2 | 5.8 | 175.1 | 600 |
| No 8 | 3.0 | 2/3 | 4.8 | 154.3 | 800 |
| PEO | — | — | 4.0 | 61.3 | 450 |

TABLE 2

High-Resolution XPS Results from the Electrospun Silk, PEO, and Silk/PEO blends Surfaces

| Element | O1s Binding Energy | O1s atom % | N1s Binding Energy | N1s Atom % | C1s Binding Energy | C1s atom % | N1s/C1s | Silk/PEO W/w |
|---|---|---|---|---|---|---|---|---|
| PEO | 531.2 | 37.4 | — | — | 284.6 | 62.6 | — | 0/100 |
| Silk | 530.3 | 24.7 | 398.4 | 18.9 | 284.6 | 56.4 | 0.33 | 100/0 |
| No. 1 | 530.9 | 27.1 | 398.5 | 15.3 | 284.6 | 57.6 | 0.26 | 79/21 |
| No. 1w20 | 531.0 | 23.6 | 399.1 | 17.3 | 284.6 | 57.9 | 0.32 | 97/3 |
| No. 1w37 | 531.3 | 23.7 | 399.3 | | 284.6 | 59.0 | 0.29 | 88/12 |
| No. 2 | 530.9 | 26.5 | 398.6 | 15.0 | 284.6 | 58.5 | 0.26 | 79/21 |
| No. 2w20 | 530.9 | 22.4 | 399.1 | 17.8 | 284.6 | 59.8 | 0.30 | 91/9 |
| No. 2w37 | 531.1 | 24.0 | 399.2 | 17.7 | 284.6 | 58.3 | 0.30 | 91/9 |
| No. 3 | 531.1 | 25.2 | 398.9 | 16.4 | 284.6 | 58.4 | 0.28 | 85/15 |
| No. 3w20 | 530.7 | 25.2 | 399.0 | 18.2 | 284.6 | 56.6 | 0.32 | 97/3 |
| No. 3w37 | 531.1 | 23.2 | 399.0 | 16.3 | 284.6 | 60.5 | 0.27 | 82/18 |
| No. 5 | 530.8 | 28.4 | 398.6 | 13.8 | 284.6 | 57.8 | 0.24 | 73/27 |
| No. 5w20 | 531.0 | 25.1 | 399.0 | 16.3 | 284.6 | 58.6 | 0.28 | 85/15 |
| No. 5w37 | 531.2 | 23.9 | 399.3 | 16.8 | 284.6 | 59.3 | 0.28 | 85/15 |
| No. 6 | 530.5 | 26.4 | 398.4 | 15.8 | 284.6 | 57.8 | 0.27 | 82/18 |
| No. 6w20 | 530.1 | 24.0 | 398.3 | 17.6 | 284.6 | 58.4 | 0.30 | 91/9 |

TABLE 2-continued

High-Resolution XPS Results from the Electrospun
Silk, PEO, and Silk/PEO blends Surfaces

| Element | O1s Binding Energy | atom % | N1s Binding Energy | Atom % | C1s Binding Energy | atom % | N1s/C1s | Silk/PEO W/w |
|---|---|---|---|---|---|---|---|---|
| No. 6w37 | 531.3 | 23.2 | 399.3 | 17.4 | 284.6 | 59.4 | 0.29 | 88/12 |
| No. 7 | 530.7 | 26.4 | 398.4 | 14.2 | 284.6 | 59.4 | 0.24 | 73/27 |
| No. 7w20 | 530.9 | 24.5 | 399.1 | 17.7 | 284.6 | 57.8 | 0.31 | 94/6 |
| No. 7w37 | 530.9 | 23.5 | 398.9 | 17.9 | 284.6 | 58.6 | 0.31 | 94/6 |
| No. 8 | 531.1 | 29.2 | 398.5 | 10.1 | 284.6 | 60.7 | 0.17 | 51/49 |
| No. 8w20 | 530.8 | 24.2 | 398.9 | 16.7 | 284.6 | 59.1 | 0.28 | 85/15 |
| No. 8w37 | 530.8 | 24.9 | 398.5 | 17.5 | 284.6 | 57.6 | 0.30 | 91/9 |

TABLE 3

High-Resolution XPS Results from the Electrospun Silk/PEO Blends Surfaces

| Element | O1s Binding Energy (eV) | Atom % | N1s Binding Energy (eV) | Atom % | C1s Binding Energy (eV) | atom % | N1s/C1s |
|---|---|---|---|---|---|---|---|
| BM[1] | 530.9 | 24.3 | 398.6 | 14.4 | 284.6 | 61.3 | 0.23 |
| AM[2] | 530.9 | 24.7 | 398.8 | 16.4 | 284.6 | 58.9 | 0.28 |
| EX2[3] | 530.9 | 24.4 | 398.9 | 17.8 | 284.6 | 57.8 | 0.31 |
| EX7[4] | 530.8 | 24.1 | 398.4 | 18.0 | 284.6 | 57.9 | 0.31 |

[1]BM: before methanol treatment,
[2]AM: after methanol treatment,
[3]EX: after PEO extraction in water for 2 days,
[4]after PEO extraction in water for 7 days.

TABLE 4

Silk fibroin/PEG or silk fibroin/PEO blend composition

| Silk fibroin stock solution (wt %) | PEG stock solution (wt %) | PEO stock solution (wt %) | Silk/PEG or PEO weight ratio in blend | Silk/PEG Blend Conc. (wt %) | Silk/PEO Blend Conc. (wt %) | Blend Ratio Silk/PEG or PEO (wt/wt) |
|---|---|---|---|---|---|---|
| 8.0 | — | — | 8.0/0 | 8.0 | 8.0 | 98/2 |
| 8.0 | 10.0 | 4.0 | 8.0/0.16 | 8.0 | 7.8 | 98/2 |
| 8.0 | 10.0 | 4.0 | 8.0/0.89 | 8.2 | 7.3 | 90/10 |
| 8.0 | 10.0 | 4.0 | 8.0/2.00 | 8.3 | 6.7 | 80/20 |
| 8.0 | 10.0 | 4.0 | 8.0/3.43 | 8.5 | 6.1 | 70/30 |
| 8.0 | 10.0 | 4.0 | 8.0/5.33 | 8.7 | 5.7 | 60/40 |

TABLE 5

Weights (mg) of silk and silk blend films before and after PEG or PEO extraction at 37° C. for 48 hrs.

| Silk/PEG or PEO Blend | Extraction Time (hr) | Silk/PEO Before | Silk/PEO After | Silk/PEG Before | Silk/PEG After |
|---|---|---|---|---|---|
| 100/0 | 12 | 96.2 | 95.6 | —[2] | — |
|  | 24 | 89.2 | 88.6 | — | — |
|  | 48 | 106.8 | 105.2 | — | — |
| 98/2 | 12 | 82.2 | 80.6 (80.9)[1] | 67.2 | 64.2 (65.8) |
|  | 24 | 76.7 | 75.5 (75.2) | 40.4 | 39.5 (39.6) |
|  | 48 | 95.7 | 91.2 (93.8) | 45.6 | 41.4 (44.7) |
| 90/10 | 12 | 79.4 | 70.0 (71.5) | 66.6 | 46.9 (59.9) |
|  | 24 | 79.1 | 70.6 (71.2) | 74.0 | 66.4 (66.6) |
|  | 48 | 74.1 | 64.3 (66.7) | 76.4 | 67.9 (68.8) |
| 80/20 | 12 | 59.2 | 51.1 (47.4) | 58.9 | 49.0 (47.1) |
|  | 24 | 54.1 | 46.7 (43.3) | 58.6 | 47.4 (46.9) |
|  | 48 | 53.8 | 45.5 (43.0) | 58.8 | 46.5 (47.0) |
| 70/30 | 12 | 66.2 | 52.2 (46.3) | 90.0 | 59.7 (63.0) |
|  | 24 | 74.2 | 58.3 (51.9) | 114.2 | 79.5 (79.9) |
|  | 48 | 59.8 | 45.6 (41.9) | 69.3 | 49.2 (48.5) |
| 60/40 | 12 | 57.8 | 39.8 (34.7) | — | — |
|  | 24 | 63.8 | 42.5 (38.3) | — | — |
|  | 48 | 51.7 | 33.6 (31.0) | — | — |

[1]Parenthesis: calculated silk weight from the blend films.
[2]Not measured.

TABLE 6

High-Resolution XPS Results from the Silk, PEO, and Silk/PEO blend film surfaces before and after methanol treatment.

| Element | O1s Binding Energy (eV) | Atom % | N1s Binding Energy (eV) | Atom % | C1s Binding Energy (eV) | atom % | N1s/C1s | Silk/PEO |
|---|---|---|---|---|---|---|---|---|
| Silk | 530.3 | 24.6 | 398.4 | 14.9 | 284.6 | 60.5 | 0.25 | 100/0 |
| PEO02B | 530.9 | 24.2 | 398.5 | 14.4 | 284.6 | 61.4 | 0.23 | 92/8 |
| PEO10B | 530.9 | 29.0 | 398.6 | 10.0 | 284.6 | 61.0 | 0.16 | 64/36 |
| PEO20B | 531.1 | 25.3 | 398.9 | 12.4 | 284.6 | 62.3 | 0.20 | 80/20 |
| PEO30B | 530.8 | 25.1 | 398.6 | 13.0 | 284.6 | 61.9 | 0.21 | 84/16 |
| PEO40B | 530.5 | 24.6 | 398.4 | 12.0 | 284.6 | 63.4 | 0.19 | 76/24 |
| PEO02A | 530.7 | 23.8 | 398.4 | 13.4 | 284.6 | 62.8 | 0.21 | 84/16 |
| PEO10A | 531.1 | 23.7 | 398.5 | 11.4 | 284.6 | 64.9 | 0.17 | 68/32 |
| PEO20A | 530.5 | 29.3 | 398.4 | 7.4 | 284.6 | 63.3 | 0.12 | 48/52 |
| PEO30A | 530.7 | 18.3 | 398.4 | 9.5 | 284.6 | 72.2 | 0.13 | 52/48 |
| PEO40A | 531.1 | 27.0 | 398.5 | 6.4 | 284.6 | 66.6 | 0.10 | 40/60 |

TABLE 7

Contact angle measurement of silk and silk/PEO blend films after methanol treatment

| Sample | SILKAM | PEO02AM | PEO10AM | PEO20AM | PEO30AM | PEO40AM |
|---|---|---|---|---|---|---|
| Angle(°) | 81 ± 2 | 76.2 ± 2 | 72.2 ± 1 | 68.0 ± 1 | 68.0 ± 1 | 63.3 ± 2 |

TABLE 8

Mechanical properties of the silk and silk/PEO blend films before and after methanol treatment

| Sample | Tensile Modulus (GPa) | Tensile Strength (MPa) | Elongation at Break (%) |
|---|---|---|---|
| SILKBM | 3.9 ± 0.7 | 47.2 ± 6.4 | 1.9 ± 0.7 |
| PEO02BM | 3.3 ± 0.6 | 63.0 ± 8.7 | 5.7 ± 2.0 |
| PEO10BM | 3.2 ± 0.2 | 42.5 ± 2.0 | 2.7 ± 0.6 |
| PEO20BM | 2.7 ± 0.3 | 28.9 ± 2.8 | 1.9 ± 0.7 |
| PEO30BM | 2.3 ± 0.1 | 29.5 ± 0.9 | 6.2 ± 1.8 |
| PEO40BM | 2.0 ± 0.03 | 32.6 ± 3.4 | 10.9 ± 4.5 |
| SILKAM | 3.5 ± 0.9 | 58.8 ± 16.7 | 2.1 ± 0.4 |
| PEO02AM | 3.4 ± 0.1 | 58.5 ± 6.5 | 3.2 ± 1.0 |
| PEO10BM | 3.2 ± 0.1 | 43.3 ± 4.7 | 2.6 ± 0.3 |
| PEO20BM | 2.3 ± 0.2 | 27.9 ± 3.0 | 2.1 ± 0.2 |
| PEO30BM | 2.1 ± 0.2 | 29.2 ± 5.3 | 4.9 ± 1.6 |
| PEO40BM | 1.4 ± 0.2 | 26.5 ± 2.3 | 8.2 ± 1.3 |

What is claimed is:

1. A composition comprising a therapeutic agent and an aqueous solution of a silk fibroin obtained from silkworm silk or spider silk comprising a biocompatible polymer, wherein the aqueous solution of silk fibroin is free of solvents other than water.

2. The composition of claim 1, wherein the aqueous solution has a shear rate from 24.3 to 1216 per second at room temperature.

3. The composition of claim 1, wherein the aqueous solution has a conductivity of 19820 siemens at room temperature.

4. A composition comprising (i) fibroin obtained from silkworm silk or spider silk, (ii) a therapeutic agent and (iii) a biocompatible polymer selected from polyethylene oxide, fibronectin, polyaspartic acid, polylysine, pectin, dextrans, and combinations of two or more thereof, wherein the composition if free of solvents other than water.

5. The composition of claim 4, further comprising an aqueous solution.

6. The composition of claim 4, wherein the therapeutic agent is selected from the group consisting of antiinfectives, chemotherapeutic agents, anti-rejection agents, analgesics and analgesic combinations, anti-inflammatory agents, hormones and growth factors.

7. The composition of claim 4, wherein the therapeutic agent is selected from the group consisting of antibiotics, antiviral agents, steroids, bone morphogenic proteins, bone morphogenic-like proteins, epidermal growth factor, fibroblast growth factor, platelet derived growth factor, insulin-like growth factor, transforming growth factors and vascular endothelial growth factor.

8. The composition of claim 4, wherein the therapeutic agent is selected from proteins, polysaccharides, glycoproteins and lipoproteins.

9. The composition of claim 4, further comprising one or more additives.

10. The composition of claim 4, wherein the therapeutic agent is mixed with the biocompatible polymer.

11. The composition of claim 4, wherein the therapeutic agent is coated on to the composition.

12. The composition of claim 4, wherein the amount of therapeutic agent is about 0.001 percent to about 70 percent of the composition.

13. The composition of claim 4, wherein the therapeutic agent is released upon contact with a body fluid.

14. The composition of claim 4, wherein the biocompatible polymer is polyethylene oxide.

15. The composition of claim 4, wherein the composition is a fiber, a film, a foam or a mat.

16. A method for delivering a therapeutic agent comprising administering the composition of claim 4 to a patient in need thereof.

17. A method for repairing a wound comprising administering the composition of claim 4 to a patient in need thereof.

18. The composition of claim 4, wherein the therapeutic agent is selected from proteins, polysaccharides, glycoproteins and lipoproteins.

19. The compositions of claim 4, wherein the therapeutic agent is present as a liquid of a finely divided solid.

* * * * *